United States Patent
Cheng et al.

(10) Patent No.: US 8,178,318 B2
(45) Date of Patent: *May 15, 2012

(54) METHOD FOR CONTROLLING PH, OSMOLALITY AND DISSOLVED CARBON DIOXIDE LEVELS IN A MAMMALIAN CELL CULTURE PROCESS TO ENHANCE CELL VIABILITY AND BIOLOGIC PRODUCT YIELD

(75) Inventors: Alan T. Y. Cheng, Naperville, IL (US); Ying Zhou, Naperville, IL (US); Amitabh Gupta, Naperville, IL (US); Balazs Hunek, Chicago, IL (US); Nigel Grinter, Buffalo Grove, IL (US)

(73) Assignee: Praxair Technology, Inc., Danbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/702,428

(22) Filed: Feb. 9, 2010

(65) Prior Publication Data

US 2010/0184147 A1   Jul. 22, 2010

Related U.S. Application Data

(63) Continuation-in-part of application No. 12/536,577, filed on Aug. 6, 2009, now abandoned.

(60) Provisional application No. 61/086,665, filed on Aug. 6, 2008, provisional application No. 61/086,685, filed on Aug. 6, 2008.

(51) Int. Cl.
*C12P 21/02* (2006.01)
(52) U.S. Cl. ............... 435/69.1; 435/394; 435/286.1; 435/287.1
(58) Field of Classification Search .................. None
See application file for complete search history.

(56) References Cited

U.S. PATENT DOCUMENTS

| | | | |
|---|---|---|---|
| 2,530,814 A | 11/1950 | Becze et al. | |
| 6,368,819 B1 * | 4/2002 | Gaddy et al. | 435/42 |
| 2003/0190710 A1 * | 10/2003 | deVries et al. | 435/70.21 |
| 2008/0108553 A1 * | 5/2008 | Luan et al. | 514/2 |
| 2009/0280565 A1 | 11/2009 | Jolicoeur et al. | |

FOREIGN PATENT DOCUMENTS

| | | |
|---|---|---|
| DE | 10 2008 103 899 A1 | 9/2009 |
| WO | WO 2010/017338 A1 | 2/2010 |

OTHER PUBLICATIONS

Jolicoeur, M. et al., "Development of a Helical-Ribbon Impeller Bioreactor for High-Density Plant Cell Suspension Culture", *Biotechnology and Bioengineering*, vol. 39, pp. 511-521 (1992). XP-002548862.

Dezengotita, V.M., et al., "Effects of $CO_2$ and osmolality on hybridoma cells: growth, metabolism and monoclonal antibody production", *Cytotechnology*, vol. 28, No. 1-3, pp. 213-227 (1998). XP-019236586.

De Dobbeleer, C., et al., "A High-Rate Perfusion Bioreactor for Plant Cells", *Biotechnology and Bioengineering*, vol. 95, No. 6, pp. 1126-1137 (2006). XP-003015870.

Kimura, R., et al., "Effects of Elevated $pCO_2$ and/or Osmolality on the Growth and Recombinant tPA Production of CHO Cells", *Biotechnology and Bioengineering*, vol. 52, No. 1, pp. 152-160 (1996). XP-002536930.

Nienow, A.W., "Reactor engineering in large scale animal cell culture", *Cytotechnology*, vol. 50, No. 1-3, pp. 9-33 (2006). XP-019393910.

Zhu, M.M., et al., "Effects of Elevated $pCO_2$ and Osmolality on Growth of CHO Cells and Production of Antibody-Fusion Protein B1: A Case Study", *Biotechnology Progress*, vol. 21, No. 1, pp. 70-77 (2005). XP-002536931.

Mostafa, S. S. et al., "Strategies for Improved dCO2 Removal in Large-Scale Fed-Batch Cultures", Biotechnology Progress, American Institute of Chemical Engineers, U.S. vol. 19, Jan. 1, 2003, pp. 45-51, XP002316576, ISSN: 8756-7938, DOI: DOI:10.1021/BP0256263.

* cited by examiner

*Primary Examiner* — Jim Ketter
(74) *Attorney, Agent, or Firm* — Robert J. Hampsch

(57) ABSTRACT

Methods for controlling the level of dissolved carbon dioxide and limiting osmolality in a mammalian cell culture process to enhance cell growth, viability and density, and increase biologic product concentration and yield are provided. Such control of the level of dissolved carbon dioxide and pH as well as the resulting ability to limit osmolality in a mammalian cell culture process is achieved by adopting alternative pH control strategies and $CO_2$ stripping techniques during a mammalian cell culture process. Such pH control techniques and carbon dioxide stripping occur without foam and with little or no damage to the mammalian cells.

21 Claims, 23 Drawing Sheets

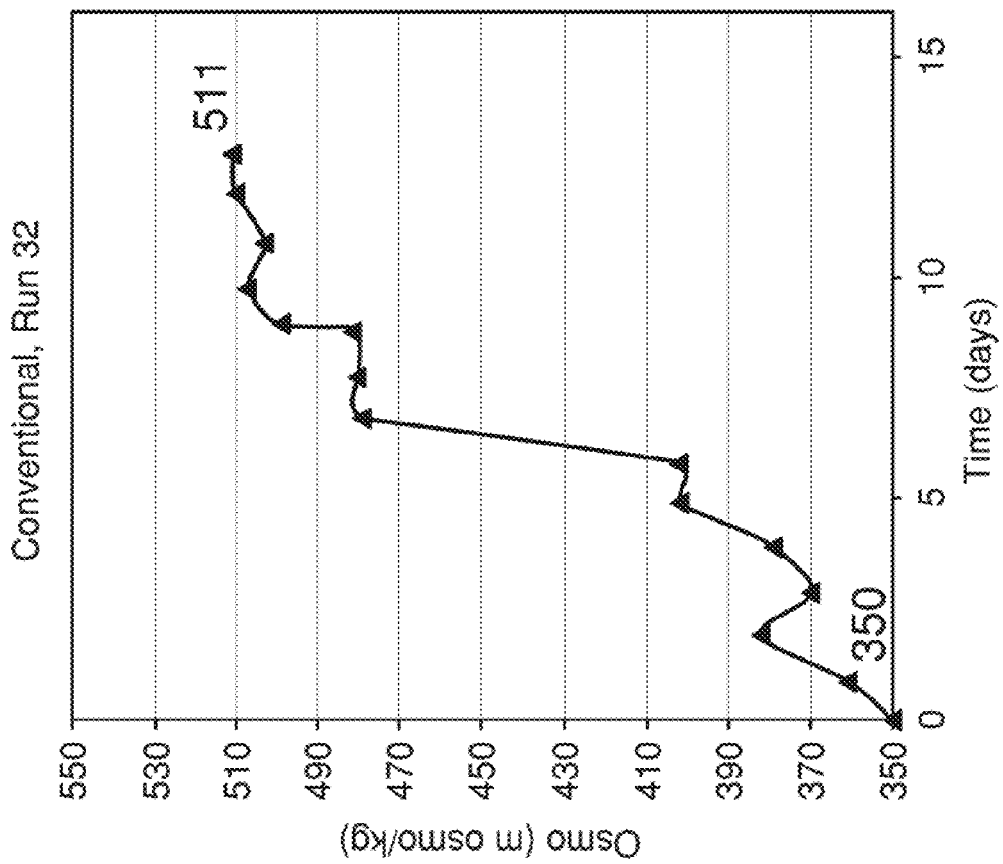
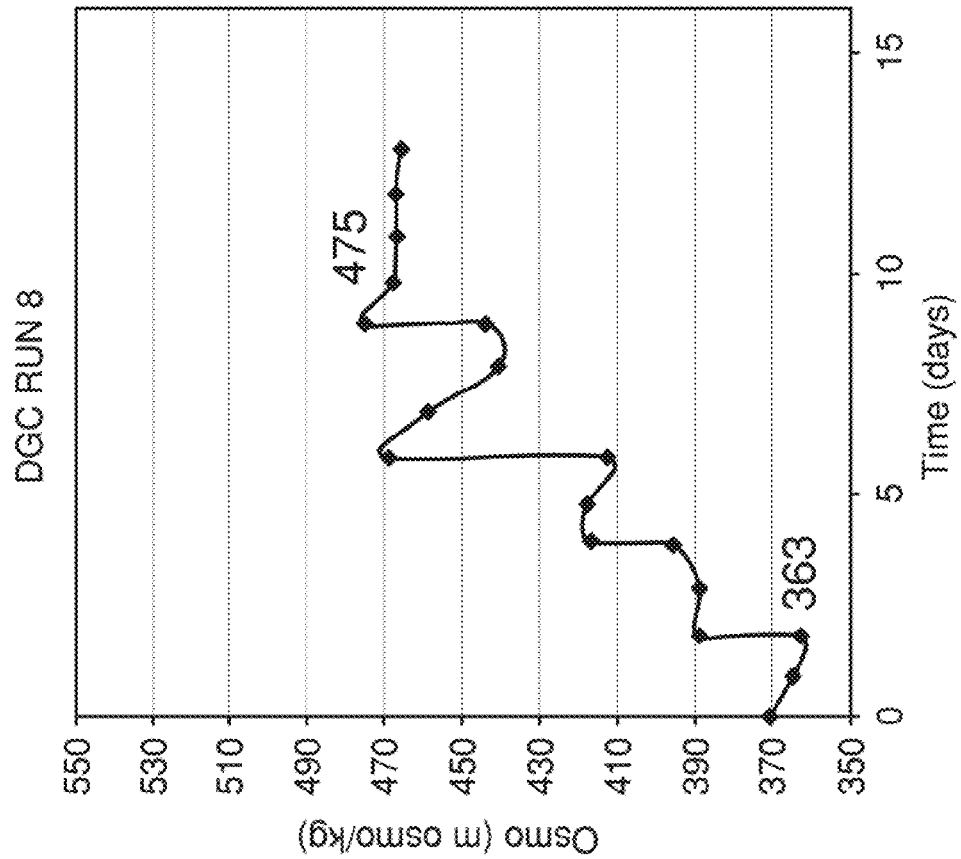

| Low dCO2 & High Osmolality | | | | | | |
|---|---|---|---|---|---|---|
| Run | dCO2 | SdCO2 | Osmo | Cell D | IgG | SP |
| 48 | 6.00 | 4.71 | 659 | 3.0 | 1,200 | 42.7 |
| 55 | 4.50 | 2.92 | 699 | 2.5 | 1,149 | 63.7 |
| Low dCO2 & Moderate Osmolality | | | | | | |
| Run | dCO2 | SdCO2 | Osmo | Cell D | IgG | SP |
| 42 | 5.80 | 2.54 | 506 | 9.3 | 2,388 | 32.2 |
| 52 | 3.70 | 2.51 | 485 | 9 | 2,012 | 48.3 |
| Low dCO2 & Low Osmolality | | | | | | |
| Run | dCO2 | SdCO2 | Osmo | Cell D | IgG | SP |
| 44 | 2.70 | 2.25 | 408 | 9.4 | 1,476 | 26.0 |
| 47 | 3.58 | 2.42 | 431 | 9.3 | 1,418 | 34.3 |
| Moderate dCO2 & High Osmolality | | | | | | |
| Run | dCO2m | SdCO2 | Osmo | Cell D | IgG | SP |
| 37 | 9 | 11.11 | 559 | 5.6 | 607 | 27.0 |
| 38 | 9.3 | 8.6 | 656 | 7.1 | 654 | 23.9 |
| Moderate dCO2 & Moderate Osmolality | | | | | | |
| Run | dCO2m | SdCO2 | Osmo | Cell D | IgG | SP |
| 29 | 10.5 | 12.2 | 436 | 11.0 | 1,294 | 22.1 |
| 30 | 13.1 | 10.46 | 439 | 13.9 | 1,266 | 18.9 |
| 32 | 15.3 | 12.6 | 503 | 10.2 | 1,183 | 19.2 |
| Moderate dCO2 & Low Osmolality | | | | | | |
| Run | dCO2m | SdCO2 | Osmo | Cell D | IgG | SP |
| 43 | 15.5 | 6.49 | 394 | 9.8 | 1,476 | 29.8 |
| High dCO2 & High Osmolality | | | | | | |
| Run | dCO2m | SdCO2 | Osmo | Cell D | IgG | SP |
| 34 | 34 | 8.51 | 535 | 4.7 | 566 | 20.7 |
| 35 | 34 | 10.76 | 559 | 5.6 | 688 | 22.3 |
| 36 | 30 | 12.16 | 601 | 4.5 | 632 | 28.8 |
| 56 | 35 | 12.92 | 660 | 2.5 | 646 | 65.3 |
| High dCO2 & Moderate Osmolality | | | | | | |
| Run | dCO2m | SdCO2 | Osmo | Cell D | IgG | SP |
| 40 | 33.7 | 7.53 | 503 | 8.7 | 745 | 16.2 |
| 59 | 30 | 14.32 | 553 | 3 | 1,040 | 55.9 |
| High dCO2 & Low Osmolality | | | | | | |
| Run | dCO2m | SdCO2 | Osmo | Cell D | IgG | SP |
| 33 | 20 | 11.1 | 426 | 2.3 | 426 | 28.8 |

FIG. 18

METHOD FOR CONTROLLING PH, OSMOLALITY AND DISSOLVED CARBON DIOXIDE LEVELS IN A MAMMALIAN CELL CULTURE PROCESS TO ENHANCE CELL VIABILITY AND BIOLOGIC PRODUCT YIELD

CROSS REFERENCE TO RELATED APPLICATIONS

The present application is a continuation-in-part application from U.S. patent application Ser. No. 12/536,577 filed Aug. 6, 2009 now abandoned and claims priority thereto and from U.S. provisional patent application Ser. Nos. 61/086,665 and 61/086,685 both filed Aug. 6, 2008, the disclosures of which are incorporated by reference herein.

FIELD OF THE INVENTION

The present invention relates to mammalian cell culture processes, and more particularly to methods for enhancing cell growth, cell density, cell viability, product concentration and product yield through improved control of process parameters including pH, osmolality and dissolved carbon dioxide level of the cell culture medium.

BACKGROUND

Commercial production of protein therapeutics and other biological products such as monoclonal antibodies is presently carried out generally in bioreactors adapted for culturing suspensions of genetically optimized mammalian, insect or other cell types. Mammalian cell culture bioreactors typically have several hundred to several thousand liters in working volume. Most common full scale manufacturing plants have bioreactors with working volumes ranging from approximately 1,000 liters up to 25,000 liters. Drug candidates for clinical trials are produced in laboratory scale bioreactors having five (5) liters to several hundred liters of working volume.

The optimization to achieve the highest biological product yields possible in the smallest amount of time and the related challenges of bioreactor scale-up have focused on the control of recognized critical process parameters such as pH, dissolved oxygen (DO), temperature, nutrient composition and by-product profiles, agitation profile, gas sparging method, nutrient feed and product harvest profiles. The importance of other process parameters such as dissolved carbon dioxide ($dCO_2$) and osmolality (i.e. concentration of dissolved particles per kilogram of solution) is just recently being documented in the literature. As a matter of fact, many commercial bioreactors do not even have the means installed to measure dissolved carbon dioxide levels and/or osmolality in-situ, let alone a means to control and optimize those parameters. Depending on the scale of the commercial operation—ranging from hundreds up to 25,000 liters of bioreactor volume—scale-up, optimization and control of the process pose different challenges. At commercial scales above about 1,000 liters, simultaneous and independent control of dissolved carbon dioxide levels and osmolality becomes difficult if not impossible with current best available technologies and methodologies.

Before a manufacturing-scale mammalian cell cultivation process starts in a bioreactor, a seed culture inoculum is typically prepared. This involves culturing production cells in a series of flasks in incubators and/or smaller bioreactors of increasing volume until enough cells are available for inoculation into the production bioreactor. The process involves transferring a cell population from one culture vessel to a larger one. Generally, a 20% dilution of the cell population is used for each transfer or subculture. In the incubator, the flasks with culture medium are clamped to a rotating platform to swirl the culture and facilitate gas transfer between the culture medium and the atmosphere in the incubators. Typically, the incubator for a mammalian cell culture process is set at 37° C. with 5% carbon dioxide ($CO_2$) and a humidity level higher than about 80%. Similar temperatures and $CO_2$ levels are used for seed cultures grown in bioreactors. When the seed culture reaches a sufficient volume and cell density, it is inoculated into the production bioreactor.

After seed culture is inoculated into the bioreactor medium, parameters such as pH, temperature, and level of dissolved oxygen are controlled to the prescribed levels during the cell cultivation process. pH is typically controlled by adding basic or acidic solutions when necessary during the process. Commonly used base solutions include sodium bicarbonate, sodium carbonate and sodium hydroxide solutions. Dissolution of carbon dioxide ($CO_2$) is commonly used to achieve a more acidic pH. Although other acids are available for controlling pH, the dissolved $CO_2$ and sodium bicarbonate combination forms a most stable and favorable buffer system for the cell culture. The preferred temperature of the culture medium or solution for mammalian cell cultivation processes is about 37° C. The desired level of dissolved oxygen in the culture medium or solution is typically achieved through air sparging using sparger installed on the bottom of the bioreactor, along with agitation of the culture medium or solution using impellers which breakup the large air/oxygen bubbles to enhance the transfer of oxygen to the cell medium from the sparged air bubbles. Purging the bioreactor headspace with a cover gas provides a limited degree of surface gas exchange. Disadvantageously, air-sparging and agitation of the culture medium or solution may result in foaming and shear damage to the mammalian cells which adversely impacts cell viability. Accumulations of foam on the surface of the culture medium also serve to further limit surface gas exchange and to reduce the available working volume of the bioreactor.

Commercial-scale mammalian cell cultivation processes may be conducted in three different operation modes: batch mode or fed-batch mode for suspended cell cultures, and perfusion mode for immobilized cells. The majority of the commercial-scale mammalian cell cultivation processes are operated in fed-batch mode. In fed-batch mode, additional media and nutrients are added to the bioreactor at different times during the cell cultivation process to supplement the carbon source and other nutrients after initial bioreactor setup.

Before any bioreactor is used for mammalian cell cultivation, it typically must be sterilized and equipped with various probes as well as connections for supplemental gas supply and introduction of additional feeds. Temperature probes, pH detectors, dissolved oxygen probes and dissolved $CO_2$ probes or sensors are used to monitor the temperature, pH, dissolved oxygen and dissolved $CO_2$ levels of the cell medium or solution in real time. In addition, cell culture medium or solution samples can be withdrawn from the bioreactor at selected intervals to determine cell density and cell viability, as well as to analyze other characteristics such as metabolites and osmolality. Based on such analytical results, additional feed or other additives can be added to the cell culture medium or solution in an effort to prolong the cell viability and increase production of biological products. When cell viability reaches a prescribed lower threshold, the cell cultivation process can be stopped or shut down. The prescribed lower threshold is often determined empirically based on the results of down-stream recovery and purification of the harvested biological products.

During the cultivation process, the mammalian cells exhibit three phases, namely the lag phase, the exponential growth phase, and the stationary or production phase. The lag phase occurs immediately after inoculation and is generally a period of physiological adaptation of mammalian cells to the new environment. After the lag phase, the mammalian cells are considered in the exponential growth phase. In the exponential growth phase, the mammalian cells multiply and cell density increases exponentially with time. Many cells actually start to produce the desired protein, antibody or biological product during some point in the exponential growth phase. Cell density refers to the total number of cells in culture, usually indicated in the density of viable and non-viable cells. When the mammalian cells reach the stationary or production phase, the viable cells are actively producing the biological products for downstream harvesting. During this phase, the total cell density may remain generally constant, but the cell viability (i.e. the percentage of viable cells) tends to decrease rapidly over time.

Mammalian cells are known to be sensitive to the amount of dissolved carbon dioxide in the cell culture media or solution. Mammalian cell cultures exposed to excess carbon dioxide levels during the exponential growth phase may demonstrate reduced production of monoclonal antibodies or other desired biological products. Before inoculation, the pH of the slightly alkaline culture media has to be lowered with carbon dioxide adjusted to an optimum value. This often leads to elevated levels of dissolved carbon dioxide at the beginning of the lag phase of many mammalian cell culture processes.

Dissolved carbon dioxide in mammalian cell culture bioreactors originates from chemical and biological sources. The chemical source of carbon dioxide is equilibrium chemical reactions occurring within the cell culture medium or solution that includes a selected amount of a buffer solution containing sodium bicarbonate and/or sodium carbonate. Additionally, carbon dioxide may be directly sparged into the slightly alkaline culture medium or solution to reduce the pH of the broth to a prescribed level, usually around 7.0, resulting in more dissolved carbon dioxide. The biological source of carbon dioxide is a product of the respiration of the mammalian cells within the bioreactor. This biological source of carbon dioxide increases with cell density and generally reaches its maximum value at about the same time that cell density within the bioreactor is maximized. However, as more carbon dioxide is produced, the pH of the cell culture medium trends toward acidic such that additional bicarbonate is needed to keep the pH of the cell culture medium or solution within the desired range.

To offset the effects of increased dissolved carbon dioxide which depresses the pH, one may add sodium bicarbonate so as to maintain the pH of the solution within the prescribed range. Both of these means to offset the effects of increased carbon dioxide have other negative consequences on the mammalian cell culture process. First, any increase in dissolved carbon dioxide levels contributes to an increase in osmolality of the cell culture medium or solution. Similarly, the addition of sodium bicarbonate, needed to adjust the pH of the solution to offset the carbon dioxide, also increases osmolality. (Osmolality represents the number of dissolved particles per kilogram of solution and is commonly reported as mOsm/kg by freeze-point depression.) The addition of sodium bicarbonate will also increase the equilibrium saturation level of dissolved carbon dioxide allowed in the solution, making carbon dioxide more difficult to be removed during the aeration process. It is known in the art that increased levels of either dissolved carbon dioxide or increased osmolality have adverse or negative impacts on cell density or yield. However, the combined or synergistic effects of carbon dioxide levels and osmolality are not well understood.

Carbon dioxide dissociates into bicarbonate ions at a pH of 7 in water. Only a fraction of the carbon dioxide remains as free $CO_2$ in an un-dissociated state. Removing the dissolved carbon dioxide from a cell culture thus becomes difficult as most mammalian cell cultures take place at pH in the range of 6.5 to 7.5. The dissociated bicarbonate ions are not easily removed and generally must be recombined into free carbon dioxide before they can be stripped out of the solution. Any addition of sodium bicarbonate to balance the pH will also increase the equilibrium dissolved carbon dioxide concentration or saturation level in the solution, making it more difficult to remove the carbon dioxide physically.

The conventional method of removing or stripping dissolved carbon dioxide from a mammalian cell culture solution is by sparging the cell culture solution with air or a gas mixture of air/oxygen/nitrogen in agitated tanks. However, gas sparging in agitated tanks results in adverse effects to the cell culture process. In particular, the gas-bubble breakage at the tip of the rotating agitator is a source of high shear rate that damages mammalian cell membranes, often sufficiently to cause cell death. Even when damage is sub-lethal, cell productivity is compromised in the period that the damaged membrane is repaired.

Also, sparging air or nitrogen into the bioreactor creates gas bubbles rising to the surface of the solution within the bioreactor where the gas is released into the headspace. Gas bubble breakage at the top surface of the cell culture solution is often more damaging to the mammalian cells than the damage caused by the agitator. Restraining the agitator speed and limiting the gas sparging rate are currently viewed as the best means to avoid such damage and increase cell viability. However, these measures reduce the amount of carbon dioxide that can be removed and the excess that cannot be removed also inhibits cell growth and viability. These disadvantages are particularly challenging to overcome in large, commercial-scale bioreactors where the shear rate goes up substantially with the diameter of the impellers. Also, the greater hydrostatic head of large scale bioreactors tends to increase the solubility of carbon dioxide, meaning that more needs to be removed to maintain dissolved $CO_2$ levels within an optimal range.

SUMMARY OF THE INVENTION

The present invention may be characterized as a method for enhancing product yield in a mammalian cell culture process comprising the step of maintaining the dissolved carbon dioxide in a cell culture medium at a level of less than about 10% concentration of dissolved carbon dioxide throughout a growth phase and a production phase of the mammalian cell culture process by removing dissolved carbon dioxide through surface gas exchange at a top surface of the cell culture medium in a bioreactor, wherein the osmolality in the cell culture medium is maintained in an optimum range for the particular cells during the mammalian cell culture process and the pH of the cell culture medium is maintained in an optimum range for the particular cells during the mammalian cell culture process.

The invention may also be characterized as a method for enhancing protein product yield in a fed-batch mammalian cell culture process comprising the steps of: (i) inoculating a mammalian cell culture in a bioreactor with a cell culture medium that has prescribed level of bicarbonate in equilibrium with dissolved carbon dioxide and an initial level of osmolality; (ii) periodically adding nutrients to the cell culture medium during a growth phase of the mammalian cell culture process; (iii) periodically adding an acid or base to the cell culture medium during the growth phase or a production phase of the mammalian cell culture process to maintain the pH level within a prescribed range for the mammalian cells without addition of carbon dioxide gas; (iv) adjusting the volumetric flow of an oxygen containing sweep gas in a headspace above a top surface of the cell culture medium in the bioreactor during the growth phase or the production phase of the mammalian cell culture process to facilitate surface gas exchange at a top surface of the cell culture medium; and (v) adjusting the rotational speed of an upward flowing impeller disposed below the top surface of the cell culture medium in the bioreactor during the growth phase or production phase. The dissolved carbon dioxide in the cell culture medium is maintained at a stable level of less than about 10% concentration of dissolved carbon dioxide throughout the growth phase or the production phase of the mammalian cell culture process by stripping carbon dioxide via the surface gas exchange. The osmolality in the cell culture medium is maintained in an optimum range for the particular cells during the mammalian cell culture process and the product yield of the fed-batch mammalian cell culture process is enhanced.

The present invention may alternatively be characterized as a method for enhancing product yield in a fed-batch mammalian cell culture process comprising the steps of: (i) inoculating the cell culture with a cell culture medium that has prescribed level of bicarbonate in equilibrium with dissolved carbon dioxide; (ii) maintaining the concentration of dissolved carbon dioxide in the cell culture medium to less than about 10% throughout a growth phase or a production phase of the fed-batch mammalian cell culture process by removing dissolved carbon dioxide; and (iii) limiting the rise of osmolality in the cell culture medium to less than 400 mOsmol/kg from the beginning of the growth phase to the end of the production phase of the fed-batch mammalian cell culture process wherein the pH of the cell culture medium is maintained in an optimum range for the particular cells during the mammalian cell culture process.

The present invention may also be characterized as a method for controlling pH level of cell culture medium in a fed-batch mammalian cell culture process comprising the steps of: (i) providing a carbon dioxide and sodium bicarbonate buffer to cell culture medium during an inoculation phase to establish a prescribed equilibrium level of bicarbonate and dissolved carbon dioxide and initial level of osmolality in the cell culture medium; (ii) stripping dissolved carbon dioxide from the cell culture medium during a growth phase and a production phase of the fed-batch mammalian cell culture process; (iii) adding nutrients to the cell culture medium during the growth phase and optionally during the production phase; (iv) adding an acid or base to the cell culture medium during the growth phase and the production phase to maintain the pH level in a prescribed range without addition of carbon dioxide gas for pH adjustment. As a result of this process, the osmolality level in the cell culture medium is maintained in a prescribed range and the rise of osmolality level from the beginning of the growth phase to the end of the production phase is less than 400 mOsmol/kg and the concentration of dissolved carbon dioxide in the cell culture medium is maintained at 10% or less during the growth phase and the production phase The present may yet alternatively be characterized as a method for extending the cell viability and increasing protein product yield during the production phase of a fed-batch mammalian cell culture process comprising the steps of: (i) diluting the cell culture medium with water during a production phase of the fed-batch mammalian cell culture process to reduce the toxic effects of waste in the cell culture medium; (ii) adding supplemental nutrients to the cell culture medium during the production phase of the fed-batch mammalian cell culture process to compensate for the dilution effect of the water; (iii) maintaining the concentration of the dissolved carbon dioxide in the cell culture medium to 10% or less and maintaining both osmolality level and pH level in the cell culture medium within an optimum range for the mammalian cells during the production phase of the fed-batch mammalian cell culture process wherein the protein product yield is increased due to the extended cell viability of the mammalian cells during the production phase of the fed-batch mammalian cell culture process.

Yet another way to characterize the present invention is as a method for improving purity of a protein product produced from a fed-batch mammalian cell culture process comprising the steps of: (i) inoculating a mammalian cell culture in a bioreactor with a cell culture medium that has prescribed level of bicarbonate in equilibrium with dissolved carbon dioxide and an initial level of osmolality; (ii) adding nutrients to the cell culture medium thereby increasing the osmolality level of the cell culture medium to accelerate protein production from the mammalian cells; (iii) adding an acid or base to the cell culture medium to maintain the pH level within a prescribed range for the mammalian cells; (iv) stripping dissolved carbon dioxide from the cell culture medium throughout the fed-batch mammalian cell culture process wherein the concentration of dissolved carbon dioxide in the cell culture medium is maintained at 10% or less wherein the rise in osmolality level from the initial level of osmolality is limited to less than about 400 mOsmol/kg; and (v) harvesting the protein product from the bioreactor during the growth phase or early production phase of the fed-batch mammalian cell culture process.

Finally, the invention may be characterized as a method of controlling the osmolality level of cell culture medium in a fed-batch mammalian cell culture process comprising the steps of: (i) providing a carbon dioxide and sodium bicarbonate buffer to cell culture medium during an inoculation phase to establish a prescribed equilibrium level of bicarbonate and dissolved carbon dioxide and initial level of osmolality in the cell culture medium; (ii) adding nutrients to the cell culture medium during a growth phase thereby increasing the osmolality level of the cell culture medium; (iii) adding an acid or base to the cell culture medium during the growth phase to maintain the pH level in a prescribed range; (iv) stripping dissolved carbon dioxide from the cell culture medium during the growth phase of the fed-batch mammalian cell culture process wherein the concentration of dissolved carbon dioxide in the cell culture medium is maintained at 10% or less during the growth phase wherein the osmolality levels in the cell culture medium decreases during portions of the growth phase and the total rise of osmolality level from the beginning of the growth phase to the end of the growth phase is less than about 400 mOsmol/kg.

BRIEF DESCRIPTION OF THE DRAWINGS

The above and other aspects, features, and advantages of the present invention will be more apparent from the following, more detailed description thereof, presented in conjunction with the following drawings, wherein:

FIG. 3B is graph that depicts the osmolality profile of typical low dissolved carbon dioxide mammalian cell culture process as described in FIGS. 1, 2 and 3A using the present Dynamic Gas Control (DGC) process.

FIG. 3C is graph that depicts the osmolality profile of a baseline mammalian cell culture process as described in FIGS. 1, 2 and 3A.

FIG. 18 is a table that provides the data collected during various cell culture process runs at various combinations of osmolality and dissolved carbon dioxide;

DETAILED DESCRIPTION

Figure 1:
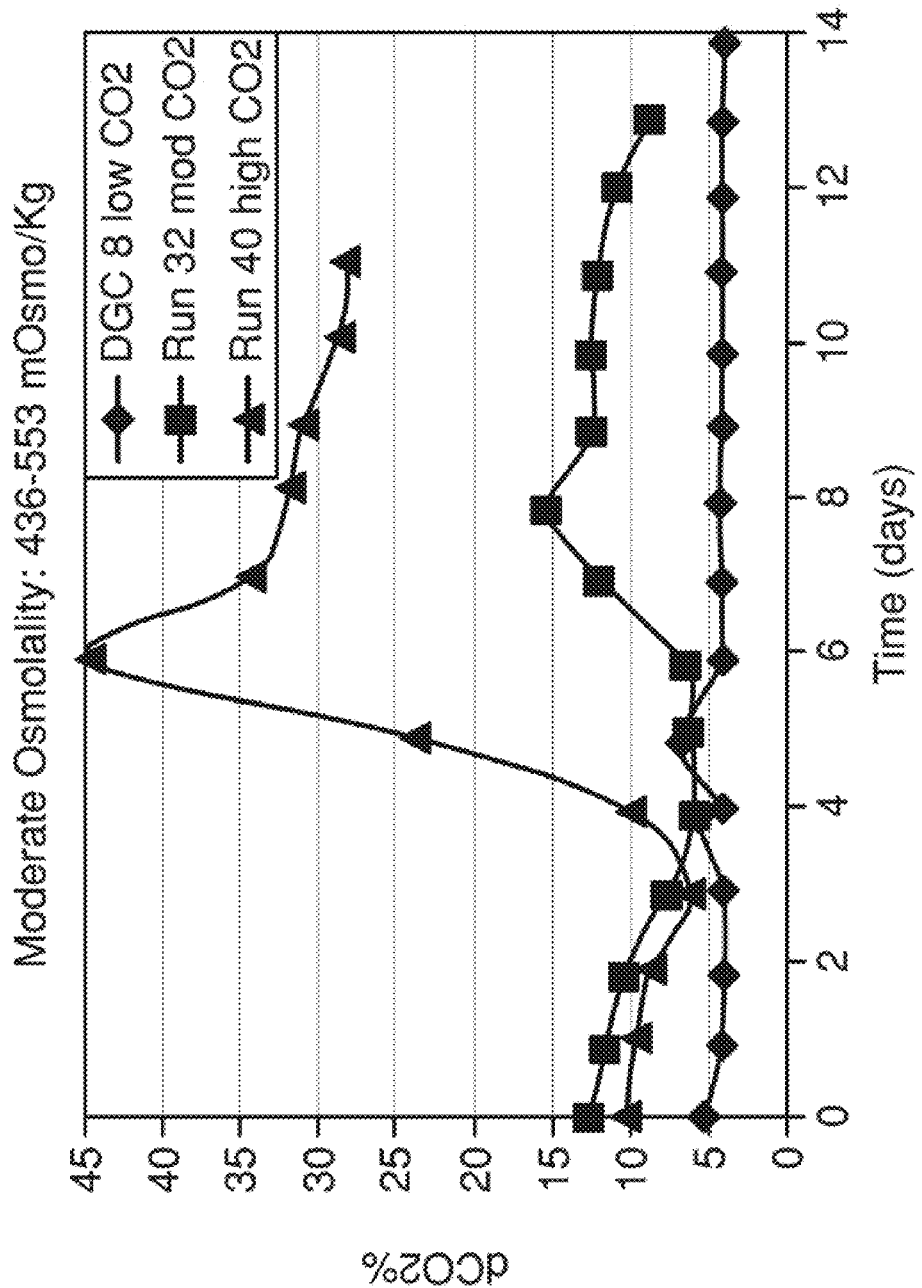
FIG. 1 is a graph that depicts percentage of dissolved carbon dioxide for three different runs of a mammalian cell line in a process having a moderate level of osmolality, wherein the three runs include one having a high peak level of dissolved carbon dioxide, another having moderate peak level of dissolved carbon dioxide, and the third having a low peak level of dissolved carbon dioxide.

Dissolved Carbon Dioxide, pH and Osmolality Relationship

With the majority of the commercial-scale mammalian cell culture manufacturing shifting to fed-batch processes, controlling to maintain a relatively constant osmolality, pH and dissolved carbon dioxide level is nearly impossible. Addition of nutrients and cell boosters during the fed-batch process will always tend to increase the cell culture osmolality, while pH and dissolved carbon dioxide levels are constantly changing throughout the process.

For example, carbon dioxide generated during the exponential growth phase can outpace the carbon dioxide stripping capacity of most current bioreactors, resulting in a continuing increase in dissolved carbon dioxide levels. This continuing rise in dissolved carbon dioxide levels often requires the addition of an alkali to neutralize the effect of the dissolved carbon dioxide on pH, since controlling the pH of the cell culture medium is viewed as one of the most critical parameters to manage in any mammalian cell culture process.

Increasing dissolved carbon dioxide and addition of alkali both further increase the osmolality of the cell culture medium or solution. In short, the pH, osmolality and dissolved carbon dioxide level in the cell culture medium or solution are all closely interrelated. Many of those skilled in the art believe lowest levels of dissolved carbon dioxide and osmolality should provide the best operating conditions of a mammalian cell culture process. However, recent studies and some empirical data disclosed herein suggest otherwise and that the optimum level of dissolved carbon dioxide and optimum osmolality still need to be determined for each separate mammalian cell line and cell culture process.

When carbon dioxide is dissolved in a mammalian cell culture medium, it forms $HCO_3^-$, an essential ion for growing cells. As the dissolved carbon dioxide establishes equilibrium with $HCO_3^-$ ions, pH is lowered. The requirement for $HCO_3^-$ is independent of its buffering action, but since carbon dioxide, $HCO_3^-$ and pH are intimately interrelated, it has been difficult to define the optimum level and direct effects of dissolved carbon dioxide on cell growth. When incubating cells in open containers, gas mixtures of 95% air and 5% carbon dioxide are typically used. The concentration of carbon dioxide was selected originally on the basis of its being that found in the alveolar spaces of the lung. This carbon dioxide concentration was intended for studies on lung fibroblasts but has now become the typical carbon dioxide concentration in mammalian cell culture processes.

The gas phase carbon dioxide tension will regulate the concentration of dissolved carbon dioxide directly, as a function of temperature. This regulation in turn produces $H_2CO_3$, which dissociates according to the reaction:

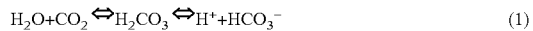

$$H_2O + CO_2 \rightleftharpoons H_2CO_3 \rightleftharpoons H^+ + HCO_3^- \quad (1)$$

$HCO_3^-$ has a fairly low dissociation constant, producing only low concentrations of hydrogen ions and achieving only a moderate lowering the solution pH. The net result of increasing atmospheric carbon dioxide is to depress pH by shifting the series of equilibria shown in (1) above to the right. To maintain a fixed pH, an alkali such as sodium bicarbonate is used to neutralize the effect of elevated carbon dioxide tension:

$$NaHCO_3 \rightleftharpoons Na^+ + HCO_3^- \quad (2)$$

The increased $HCO_3^-$ concentration counteracts the effect of higher dissolved carbon dioxide levels, pushing the equilibria in (1) above leftwards until equilibrium can be established at pH 7.4 for the bicarbonate system.

In summary, cell cultures in open vessels need to be incubated in an atmosphere of carbon dioxide, the concentration of which is in equilibrium with the sodium bicarbonate in the medium. Cells grown in sealed flasks to moderately high concentrations ($1 \times 10^5$ cells/ml) may not need carbon dioxide added to the gas phase provided that the bicarbonate concentration is kept low (~4 mM), particularly if the cells are high acid producers. At lower cell concentrations, however (e.g., during cloning or inoculation), and with some primary cultures, it is necessary to add carbon dioxide to the gas phase of sealed flasks. When venting is required to allow either the equilibration of carbon dioxide or its escape (as with high acid producers), it is necessary to leave the cap slack or to use a carbon dioxide-permeable cap. The majority of incubators are purged with mixtures of 95% air and 5% carbon dioxide.

In well controlled bioreactors, carbon dioxide will be needed at least at the start to adjust the medium pH to the proper value. Additional carbon dioxide will be needed to neutralize inoculants grown in small containers in incubators since these tend to have a higher pH than bioreactor set points. These initial pH adjustments with carbon dioxide will raise the osmolality of the starting batch.

As the cells cultured in a batch process reach the exponential growth phase, they become maximally metabolically active and each cell produces its maximum carbon dioxide output. When the cell density is low, most of carbon dioxide can be removed by sparging the broth with air or sweeping the headspace of the bioreactor with a cover gas or air. A few days into the batch cycle, however, the carbon dioxide generation will exceed the normal carbon dioxide removal capacity of a typical bioreactor. The excess carbon dioxide generated by the cells will increase the dissolved carbon dioxide level and decrease the solution pH. In order to maintain the preferred pH, additional base has to be added, resulting in excessive dissolved carbon dioxide and undesirably high osmolality in the bioreactor broth.

The sub-optimal conditions due to imbalance between carbon dioxide generation and stripping rates become more severe with scale up to larger sized bioreactors. First, the surface-area-to-volume ratio decreases as conventional bioreactors increase in size. For the same cover gas to reactor volume, the effectiveness of carbon dioxide removal at the liquid surface is largely diminished. Examples of preferred carbon dioxide stripping systems and methods are disclosed in U.S. provisional patent application Ser. No. 61/086,665.

pH Optimization in Mammalian Cell Culture

The pH set-point in a mammalian cell culture process can significantly affect the cell-culture performance. Cell culture medium pH is known to affect intracellular enzymatic activity of many mammalian cell types. Lowering pH reduces specific glucose consumption and lactate production rates, reducing the risk of glucose depletion or toxic levels of lactate. The lower pH set point in typical mammalian cell cultures is about 7.0; a pH below about 6.8 is known to inhibit cell growth. Medium or moderate pH values also are known to affect the specific growth rate and specific production rate of mammalian cells, which ultimately affects the overall culture productivity. Excessively low or high pH can kill the cells.

A pH range of about 7.0 to 7.4 is commonly used in mammalian cell culture processes. The wide fluctuations in pH that often occur during the process as, for example, when medium is replenished have an adverse effect on the cells. Controlling pH in mammalian cell culture processes is particularly important nowadays because high cell densities ($>1 \times 10^6$ cells/ml) are routinely achieved. Without proper pH control, the cell culture broth can rapidly become acidic when cells are so concentrated.

Different types of mammalian cells may have different pH optima for growth. In general, human fibroblasts are grown at a higher pH (7.6-7.8) than established cells (pH 7.0-7.4), and it is usual to culture primary cells at a pH of 7.2-7.4. The optimum pH for growth of human foreskin fibroblasts (e.g. FS-4) at low culture densities is more alkaline than the optimum pH for growth of human lung fibroblasts (e.g. MRC-5). When culturing these cells during the growth phase at a density of about $10^5$ cells/ml or less, the pH should be about 7.7 to 7.8 for FS-4 cells and about 7.5 to 7.6 for MRC-5 cells. For CHO cells, it is normally advantageous to cultivate the cells at a pH of about 7.0 during attachment. After several hours, the pH in CHO cell culture processes can be increased to slightly higher values.

Maintaining the cell culture broth at a pH of about 7.0 or higher presents another challenge to efforts to control dissolved carbon dioxide levels. As carbon dioxide can react with water, it may exist in the liquid phase in any of four forms: $CO_2$, $H_2CO_3$, $HCO_3^-$, and $CO_3^{2-}$.

The equilibrium relations as in equation (1), above, indicated that at a pH of about 5.0 or below, nearly all dissolved carbon dioxide is in the form of $CO_2$. At a pH of between about 7.0 to 9.0, bicarbonate is the dominant form of carbon. Finally, at a pH of about 11.0 or greater, nearly all is carbonate. Since the pH of most mammalian cell cultures is generally controlled between about pH7.0 to pH7.4, carbon dioxide removal is generally more difficult when compared to microbial fermentation processes where the pH can be much lower.

To remove dissolved carbon dioxide from a cell culture broth at pH between about 7.0 and 7.4, the limiting step can be either chemical or physical. Since only the dissolved carbon dioxide molecule is transported across the gas-liquid interface, the bicarbonate must be re-associated to form carbon dioxide molecules. Separating equation (1) above into its two sections, it is noted that the reverse reaction set forth below as equations (3) and (4) is generally fast, whereas the first part of the reaction, represented by equation (5), is much slower.

$$H_2CO_3 \Leftrightarrow HCO_3^- + H^+ \quad (3)$$

$$K_{eq}(T = 28° \text{ C.}) = \frac{[H^+][HCO_3^-]}{[H_2CO_3]} = 2.5 \times 10^{-4} \text{ mol/L} \quad (4)$$

$$H_2CO_3 \underset{k_{-1}}{\overset{k_1}{\longleftrightarrow}} CO_2 + H_2O \quad (5)$$

where
$k_1 = 20 \text{ s}^{-1}$ and $k_{-1} = 0.03 \text{ s}^{-1}$

Control of pH is a key operating condition as many types of mammalian cells die when the pH is substantially outside the range between pH7.0 and pH7.4. With the limitations inherent in current cell culture process controls, the primary target is pH regulation, with dissolved carbon dioxide/bicarbonate levels and osmolality largely uncontrolled and varying significantly during the culture cycle. Few data are available demonstrating the benefits of simultaneously maintaining constant pH, dissolved carbon dioxide and osmolality.

Culture media must be buffered under two sets of cell growth conditions: (1) in small open containers (e.g., inside an incubator), wherein the carbon dioxide can be lost to the atmosphere, causing the pH to rise, and (2) in a bioreactor when maximal production of carbon dioxide and lactic acid by high cell concentrations causes pH to fall. A buffer may be incorporated into the medium to stabilize the pH, but additional gaseous carbon dioxide is still required by some cell lines, particularly at low cell concentrations, to prevent the total loss of dissolved carbon dioxide and bicarbonate from the medium.

Despite its poor buffering capacity at physiological pH, bicarbonate buffer is still used more frequently than any other buffer because of its low toxicity, low cost, and nutritional benefits to the culture. Therefore, the role of carbon dioxide in controlling pH is still the most important aspect to consider when optimizing conditions for high cell yields and high cell viability.

If another alkali (e.g., NaOH) is used instead, the net result is similar to bicarbonate:

$$NaOH + H_2CO_3 \Leftrightarrow NaHCO_3 + H_2O \Leftrightarrow Na^+ + HCO_3^- + H_2O \quad (6)$$

Because many cell culture media components are made up in acid solution and may incorporate a buffer, it is difficult to predict how much bicarbonate to use when other bases may also indirectly contribute to bicarbonate levels as in equation (6) above.

With the introduction of Good's buffers (e.g. HEPES, Tricine) into tissue culture, there is speculation that carbon dioxide would no longer be necessary to stabilize the pH, and thus could be omitted. This speculation proved to be untrue, at least for a large number of mammalian cell types, particularly at low cell concentrations. Although 20 mM HEPES has been shown to control pH within the normal physiological range, the absence of atmospheric carbon dioxide allows equation (1) to move to the left, eventually eliminating dissolved carbon dioxide, and ultimately $HCO_3^-$, from the cell culture medium. This chain of events appears to limit cell growth, although it is not clear whether the limited cell growth is a result of lack of dissolved carbon dioxide or the lack of $HCO_3^-$, or both.

Another example is the Leibovitz L-15 cell culture medium that does not utilize carbon dioxide for buffering or to control pH. Leibovitz L-15 cell culture medium is preferably used when low tensions of carbon dioxide are required. Leibovitz L-15 contains a higher concentration of sodium pyruvate (550 mg/L) but lacks $NaHCO_3$ and does not require carbon dioxide in the gas phase. The inclusion of pyruvate in the medium enables mammalian cells to increase their production of carbon dioxide, making them independent of external supplied carbon dioxide, as well as $HCO_3^-$. Buffering in the Leibovitz L-15 cell culture medium is achieved via the relatively high amino acid concentrations. However, elimination of bicarbonate from the cell culture medium has a similar negative impact on cell growth as that seen with Good's buffers described above. These types of buffer systems may work well for small open dishes with low cell densities, but would be very detrimental in high cell density bioreactors.

At present, most cell culture media utilize a $CO_2/HCO_3^-$ buffer system, but its capacity is often not sufficient to prevent pH decreasing towards the end of the cell culture cycle in small batch processes In larger scale mammalian cell cultures in bioreactors, small changes in pH can be controlled by adding $HCO_3$ or increasing the carbon dioxide tension. Adding NaOH or HCl will control larger changes, but localized cell damage can result from addition of strong base or acid. The constant monitoring and control opportunities afforded by large-scale systems mean that HEPES is no longer essential for high cell yields. Cell culture pH can also be controlled when replenishing with fresh medium. Care should be taken not to significantly change the osmolality of the cell culture medium when adding buffers for pH control.

Medium osmolality significantly affects cell-culture productivity. Increased medium osmolality has been shown to decrease specific cell-growth rate and increase specific production rate. The initial medium osmolality can be predicted from the medium formulation. The amount of interaction between medium components typically does not make the osmolality significantly different from the sum of each component's contribution. Individual osmolalities for components of a typical medium are shown in the following table.

| Medium Compositions | Osmotic Contribution (mOsm/Kg) |
| --- | --- |
| $CaCl_2$ | 19.42 |
| $CuSO_4 \cdot 5H_2O$ | 7.23 |
| KCl | 25.15 |
| MgCl | 15.00 |
| $MgSO_4$ | 5.62 |
| NaCl | 34.74 |

| Medium Compositions | Osmotic Contribution (mOsm/Kg) |
|---|---|
| NaH$_2$PO$_4$ | 18.23 |
| NaHCO$_3$ | 23.27 |
| ZnS$_4$—7H$_2$O | 8.63 |
| Glucose | 6.49 |
| L-glutamine | 6.84 |
| Amino acid pools | 8.59 |
| NaOH | 50.00 |
| Pluronic F-68 | 0.00 |
| FBS | 2.64 |

The growth and function of cells in culture depends on maintaining an appropriate osmolality in the medium. Some cells (e.g. HeLa and other established cell lines) can tolerate wide fluctuations in osmolality. In contrast, primary cells and normal diploid strains are very sensitive to changes in osmolality, and high yields can only be obtained if it is kept within a narrow range.

Controlling osmolality is reported to give more reproducible cultures. Whenever the source of a particular culture medium is changed, osmolality should be checked. Osmolality of cell culture media produced by commercial suppliers may differ, probably because of differences in interpretation of original formulations. However, high-yield cultures often require various additions to the medium during the culture cycle. These can include buffers (HEPES), acid (HCl), base (NaOH), growth hormone and nutrients. If it is necessary to raise osmolality, NaCl can be added, the correct amount required to achieve a particular osmolality is calculated as follows:

For example: 1 mg NaCl/ml=1 ml stock (mOsm)=32 mOsm increase.

$$\frac{D_{osm} - M_{osm}}{32} = X \quad (7)$$

where $D_{osm}$ = desired osmolality(mOsm)

$M_{osm}$ = measured osmolality(mOsm);

and

X = ml of stock of NaCl(mOsm) to be added per ml of medium.

The osmolality of the medium is measured and the amount of stock NaCl (1 mg/ml) that must be added to achieve the desired osmolality is calculated. Measuring osmolality by freezing point depression is the most practical method, since it does not require diluting the nutrients in the medium or adding large volumes of buffers or saline solutions. Vapor pressure depression is another popular method of measuring osmolality.

pH Control

The most common procedure to maintain pH in mammalian cell culture is to use sodium bicarbonate/carbon dioxide, a gentle buffer that gives very good protection against pH fluctuations in the bioreactor. However, the bicarbonate level dictates the equilibrium dissolved carbon dioxide level at the start of the cell culture cycle as the concentration ratio of bicarbonate to dissolved carbon dioxide is set by the rapid acid-base equilibrium. The pH in the bioreactor is thereafter controlled with further additions of bicarbonate or carbon dioxide. For example, lactic acid generation by the cell culture process would prompt further bicarbonate addition until a pH of about 7.0 is attained when the bicarbonate partially decomposes into carbon dioxide. Ammonia generated by cells during the cell culture process would prompt further carbon dioxide addition. Continually adding bicarbonate or carbon dioxide typically results in excessive osmolality in the cell culture medium as well as continual fluctuations in the dissolved carbon dioxide levels during the cell culture process.

The system and method disclosed herein for controlling pH in a mammalian cell culture process comprises ascertaining the desired pH range and desired level of dissolved carbon dioxide for the selected cell culture medium; providing an initial minimum amount of bicarbonate to adjust the pH of the cell culture medium to fall within the desired pH range and produce the desired level of dissolved carbon dioxide within the cell culture media. It was found that this initial equilibrium between dissolved carbon dioxide level and bicarbonate level has a significant impact on final cell viability and product level and yield. Enough sodium bicarbonate is added into the medium before inoculation sufficient to allow equilibrium of dissolved carbon dioxide to attain only a low level, less than 10% and more preferably about 5%.

Thereafter, pH is maintained by adding sodium hydroxide as required to maintain pH within the desired range to avoid further increase in bicarbonate and an associated increase in dissolved carbon dioxide. The sodium hydroxide—a strong base—also maintains pH within the desired range without significantly increasing the osmolality and maintains the levels of dissolved carbon dioxide relatively stably at or near the desired levels.

Controlling Dissolved Carbon Dioxide Levels to Enhance Cell Culture Process

Some prior art references suggest that the level of dissolved level carbon dioxide in the cell culture solution has little or no effect on specific growth rate and cell density during the exponential growth phase or the production phase of the cell culture process. Most of these prior art experiments were conducted in conventional stirred tank bioreactors where increasing sparging rate with gas was the only mean to move additional carbon dioxide. The death rates of the cells due to foaming and shear would mask the benefits of removing carbon dioxide.

The present system and method provides for tight control of the dissolved carbon dioxide level in the cell culture media both at start-up and during the exponential growth phase which provides a beneficial effect on cell viability during the production phase. Thus, the accumulated product yield is also influenced by the exposure of the cells to prescribed levels of dissolved carbon dioxide during the growth phase. As described herein, various test runs or test batches demonstrate that tightly controlling the level of dissolved carbon dioxide during the exponential growth phase yields higher accumulated product yield during production phase and also results in a slower degradation or reduction in cell viability during the production phase.

Exchange between gas in the bioreactor vessel headspace and that dissolved in the liquid/solution occurs at the surface of the cell culture solution. Carbon dioxide removal by this means is attractive as compared to stripping via sparged gas since it minimizes shear and bubble damage to cells and reduces or eliminates foaming. Surface gas exchange in commercial scale bioreactors is not presently exploited for carbon dioxide removal, however, since under current process conditions it is far too limited to have practical use. This is a direct consequence of the limited surface to volume ratio of typical conventional bioreactor vessels and the slow rates of culture surface renewal achieved by current agitator designs. These problems become worse in bioreactors with tall and narrow configurations.

Another disadvantage of surface gas exchange in commercial scale bioreactors occurs with the use of rotating shaft agitators. These cause the surface liquid to swirl around in a circle with little tendency for solution from deeper within the vessel to replace it. This has at least two consequences affecting surface gas exchange: first, the surface liquid layer rapidly becomes depleted of dissolved carbon dioxide, lowering the driving force for subsequent $CO_2$ removal to the headspace; second, liquid from the bottom of the bioreactor (where the concentration of dissolved $CO_2$ is greatest thanks to the higher hydrostatic pressures in this region) is only rarely driven to the surface where it can donate dissolved gas to the headspace. The overall effect is that removal of dissolved $CO_2$ is slow and that there is a gradient of dissolved $CO_2$ concentration in the bioreactor, from very low at the surface to high at the bottom where it can easily reach levels that reduce cell productivity and viability.

The present method of controlling the dissolved $CO_2$ removal employs a bioreactor system having an upward flow impeller disposed within a draft tube disposed in the bioreactor vessel. The upward pumping impeller is driven via shaft by a motor outside the bioreactor vessel. The upward flow of the impeller provides a top surface renewal method that enhances surface gas exchange in a highly controllable manner. The upward pumping impeller moves cell culture medium and suspended mammalian cells from the bottom of the bioreactor vessel toward the liquid/headspace gas interface in the upper part of the reactor. In doing so, dissolved carbon dioxide in the cell culture solution or medium is continuously and rapidly brought to the surface of the liquid in the bioreactor where gas-liquid exchange is occurring. A high turnover in the surface liquid allows rapid removal of dissolved carbon dioxide to the headspace. The upward flow impeller allows a higher pumping velocity without creating sufficient shear to damage or kill the mammalian cells. A sweeping gas consisting of oxygen, nitrogen, air, carbon dioxide or other suitable gases and mixtures thereof that is introduced to the headspace in the bioreactor vessel, where it interacts with the top surface of the solution to achieve the desired liquid gas exchange, and is subsequently exhausted from the headspace in the bioreactor vessel.

The preferred bioreactor system also may include a plurality of sensors and analyzers including a pH sensor, a $dCO_2$ sensor, a temperature indicator, a dissolved oxygen analyzer, and a vent gas analyzer. Such sensors and analyzers are coupled as inputs to a system controller (not shown) that controls or adjusts the gas supply of oxygen, nitrogen, and carbon dioxide to the bioreactor vessel. The system may also include an exhaust subsystem, a plurality of biological filters as well as a means for sterilizing the bioreactor vessel with water and steam, as needed.

The upward pumping impeller is preferably located near the middle of the main bioreactor vessel so that the impeller is submerged for low liquid medium or solution starting levels. The impeller speed is adjustable and may be varied throughout the cell culture process to maintain the desired level of dissolved carbon dioxide at all times for the particular mammalian cell culture process. Preferably, the impeller speed is maintained at very low speeds when the liquid or solution level within the bioreactor vessel is low and should be increased as the liquid or solution level rises. Preferably, a draft tube is to be added to increase the upward flowing velocity, resulting in a higher gas exchange rate. The impeller speed is preferably highest during the end of the exponential growth phase of the cell culture process, when the liquid or solution level in the bioreactor vessel is also highest. Normally, surface gas exchange is an inefficient process as the available surface area is very limited. Any gas exchange occurring between the headspace and the liquid surface will quickly result in gas concentrations on either side of the gas/liquid interface quickly approaching saturation levels. Without proper concentration driving force at the interface, surface aeration is impractical unless measures are implemented to greatly increase the surface area available for gas exchange. Unfortunately, such measures (e.g., atomization of some of the liquid) create excessive shear that would damage and kill fragile mammalian cells. The Dynamic Gas Control process overcomes those limitations, however, by rapidly sweeping the headspace gases to avoid carbon dioxide build up in the gas phase boundary layer. The limitation of the liquid phase boundary layer is also eliminated by the upward pumping action of the submerged impeller.

It was observed that a number of vertical baffles added on top of the impeller make very large improvements to the gas exchange rate. These vertical baffles translate the rotational velocity into virtually pure vertically oriented flows. To compare the effect of the draft tube and vertical baffles on the dissolved $CO_2$ removal rate through the liquid surface, a carbon dioxide removal test was conducted in a 300 L vessel using the method described in this invention. The solution in the vessel was maintained at a pH of 7 and headspace swept with air. The helical impeller was set to run at two different speeds with a frequency inverter. Dissolved $CO_2$ level was measured continuously during the experiment. The results were reported in terms of volumetric mass transfer coefficient ($K_L a$) in Table (1).

TABLE 1

| Frequency inverter (Hz) | Without Draft Tube or Baffles $K_L a$ (1/hr) | Draft Tube + Baffles $K_L a$ (1/hr) | Improvement in Mass Transfer Coefficient % |
|---|---|---|---|
| 40 | 0.85 | 6.61 | 678% |
| 30 | 1.29 | 4.2 | 226% |

Depending on the speed of the upward flowing, helical impeller, the results showed that the mass transfer coefficient improved between 226% and 678% when a draft tube with baffle was used. Further tests were conducted to show the importance of the vertical baffles on the surface gas exchange phenomena in these experiments, the helical impeller was installed in the bottom of the 300 L vessel with the vertical baffles removed. From the experimental work of this invention, it was concluded that it is critical to eliminate the swirling movement of the surface liquid (see Table 2). By eliminating swirling motion at the surface, the upward flowing liquid from the impeller emerges quickly from the impeller shaft without splashing and spreads across the entire vessel surface, re-submerging into the body of the liquid near the edge of the vessel creating a rolling surface phenomenon. With the vertical baffles installed, the carbon dioxide removal rate was improved by 28% to 128%, depending on the rotational speed of the upward flowing, helical impeller. These experimental results show that liquid from the lower part of the bioreactor rapidly replaces the surface liquid, resulting in substantially higher rates of dissolved carbon dioxide removal and oxygen dissolution into the cell culture medium. Without the vertical baffle, the swirling surface liquid is not significantly replaced by fresh liquid from deeper within the bioreactor.

TABLE 2

| Frequency inverter (Hz) | Draft Tube, w/o Baffles $K_L a$ (1/hr) | Draft Tube with Baffles $K_L a$ (1/hr) | Improvement in Mass Transfer Coefficient % |
|---|---|---|---|
| 40 | 1.37 | 3.12 | 128% |
| 30 | 1.24 | 1.98 | 60% |
| 20 | 0.8 | 1.02 | 28% |

As discussed above, the liquid or solution in the bottom of a large bioreactor vessel is exposed to significant hydrostatic pressures, and the dissolved carbon dioxide trapped inside the mammalian cells will be slow to equilibrate. The presently disclosed upward pumping impeller mitigates this problem. By recirculating liquid solution and mammalian cells from the bottom of the bioreactor vessel upward to the top surface, the mammalian cells are exposed to a lower overall average hydrostatic pressure regime and thus achieve a better equilibrium level of dissolved carbon dioxide. The continuous axial or upward recirculating of the cell culture medium or solution provides a varying level hydrostatic pressure on the mammalian cells which is believed to enhance the ability of the cells to expel excess dissolved carbon dioxide deep inside the plasma of the cells Since there are no deflecting walls or dividers in the bioreactor the upward flowing liquid can reach the top surface very rapidly before rolling outward towards the bioreactor wall. This provides a very rapid renewal of the liquid surface which promotes rapid removal of dissolved carbon dioxide. Alternate forms of impellers can be used to provide the upward recirculating flow with or without the draft tube. Preferably, the upward pumping impeller is a screw impeller or propeller. However, other propellers may also be used so long as the lateral or radial flow from the propeller is minimized which, in turn reduces shearing and other damage to the mammalian cells.

Rapid gas-liquid surface renewal is also useful for dissolving gases into the liquid. For example, the presently disclosed gas-liquid surface renewal method can be used to dissolve the prescribed amount of oxygen needed for the growing cells. When the demand for oxygen is high, the oxygen composition in the sweeping gas in the headspace is increased, resulting in increased transfer of oxygen to the top surface of the recirculating liquid. When the oxygen dissolution requirement is low, the oxygen composition in the sweeping gas in the headspace is reduced and replaced with air or nitrogen. The variation in oxygen composition of the sweeping gas has little or no impact on the carbon dioxide removal rate. The dissolved oxygen concentration is preferably maintained at about 50% in many mammalian cell culture processes. In some cases, such as recombinant protein production from virus infected sf-9 insect cell culture, very low oxygen concentrations (e.g. less than 5% oxygen concentration) are used in the cell culture solution to enhance protein production by the cells.

The dissolved carbon dioxide level can be adjusted or maintained at any desirable level. To decrease the dissolved carbon dioxide level at any time during the cell culture process, the flow rate of the sweeping gas going into the headspace of the bioreactor can be increased to more rapidly eliminate $CO_2$ from the liquid near the surface. The impeller rotational speed can also be increased to speed up the surface liquid renewal rate. To increase the dissolved carbon dioxide level, one would reduce the sweeping gas flow rate and/or decrease rotational speed of the upward pumping impeller. If additional carbon dioxide is needed as, for example, may be the case in the earliest stages of the process shortly after inoculation of the production bioreactor, it can be added to the sweeping gas mixture in the headspace as required. In typical mammalian cell culture processes, the dissolved oxygen requirement increases as the batch proceeds from the initial lag phase to the end of the exponential growth phase, while the dissolved carbon dioxide concentration increases due to cell respiration, reaches a maximum concentration towards the end of the exponential growth phase, and then is gradually reduced during the production phase. Therefore, gaseous carbon dioxide is added mostly during the lag phase to regulate and maintain pH. Also, some prescribed level of dissolved oxygen needs to be maintained during the cell production phase.

In addition to independently adjusting or controlling the nitrogen, oxygen and carbon dioxide concentrations in the sweeping gas mixture, increasing the total headspace gas flow will also avoid accumulation of the stripped gases in the headspace.

In the preferred embodiment, the gas supply of nitrogen, oxygen and carbon dioxide to the bioreactor vessel is introduced above the top surface of the liquid in the headspace and preferably closely adjacent to the rolling surface of the liquid solution in the bioreactor vessel. Such gas introduction can be achieved by making the gas injectors movable so as to always inject the gases at or near the top surface as the liquid level in the bioreactor vessel rises. Impingement of the gas at the rolling top surface reduces the momentum boundary layer on the gas side and improves the total mass transfer rate between the liquid and gas. Alternatively, the gas supply may be delivered using fixed gas injectors disposed so as to introduce the gas at a location near the maximum liquid height that will be attained in the bioreactor vessel. In most mammalian cell culture processes, the maximum liquid height in the bioreactor vessel occurs during the peak of the exponential growth phase where removal of $dCO_2$ is most necessary.

Although not preferred, controlled introduction of the gas supply of air, oxygen and carbon dioxide (for the initial adjustment of media pH) to the bioreactor vessel may be supplemented by sparging the gases within the solution using one or more spargers disposed within the bioreactor vessel. The sparger used to dissolve oxygen can have finer nozzles (or holes) to generate small oxygen bubbles that dissolve or are absorbed before breaking the liquid surface, providing the flow rate is small. Sparger is designed to generate gas bubbles in the bottom of the bioreactors so it is efficient to dissolve oxygen or carbon dioxide (for pH adjustment). However, sparger is inferior in stripping dissolved carbon dioxide as stripped carbon dioxide can quickly saturate the gas bubbles or reduce the concentration driving force at the gas-liquid interface, especially in the low flow rate. At higher flow rates, violate shear and foaming will kill the cells. Such submerged gas spargers can assist with the independent addition of oxygen in combination with the headspace gas exchange method. Using the sparger to assist dissolved carbon dioxide removal is highly undesirable but is usable to dissolve small amount of pure oxygen during high cell density. When used, the gas spargers are preferably located apart from the upward flow impeller to maximize their residence time in the cell culture medium. With small amount of pure oxygen will ever needed on top of the gas exchange on the liquid surface, the oxygen bubbles will not cause significant damages in this specific case. Furthermore, gas bubbles generated by sparging only, not by the shear action of the impellers tend to be much bigger than those injected into impellers directly, and the potential for foaming is greatly diminished. Gas exchange now occurs both on the surface and in the bulk of the liquid. Sparging small volumes of gases intermittently for short periods of time allows oxygen uptake to be maximized without resorting to very high flows of sweeping gas or employing the fastest impeller speeds. It is important that such sparging be done only at peak demand for oxygen dissolution and carbon dioxide removal in order to minimize cell damage. Although such sparging might also assist stripping of $dCO_2$, the impacts or contributions have not shown to be significant during all the cell culture runs.

The preferred upward pumping device is a helical impeller that can move large volumes of liquid upward with minimal radial flow. Using a helical impeller, carbon dioxide removal rate was measured from a simulated broth and reported as Volumetric Mass Coefficient. The higher the mass transfer coefficient, the better the gas exchange efficiency. Even with an upward pumping impeller, the moving liquid stream is going to be rotated by the rotation of the agitator. As a result, the surface liquid is going to swirl, greatly reducing liquid surface renewal as the surface liquid rotates in the plane of the surface. To stop the swirling, a vertical baffle system is also used on top of the impeller to break the rotation of the liquid and redirect the flow straight to the surface. Hence, the surface liquid radiates outwards from the shaft at the center of the vessel, spreading and thinning towards the edge of the vessel where it submerges. As a result, the surface gas exchange and carbon dioxide stripping is greatly improved.

Turning to FIGS. 1, 2A, 2B, 2C, 3A, 3B, and 3C, there are shown test data in graphical form for three different runs of a mammalian cell culture process wherein the osmolality of the cell culture solution was maintained at a moderate value (i.e. 436 to 553 mOsm/kg). Of the three samples tested, one of the samples incorporating the presently disclosed Dynamic Gas Control (DGC) technology and identified as DGC8, has a level of dissolved carbon dioxide maintained at about 4% throughout the process with a small increase to about 5.7% dissolved carbon dioxide on Day 5. A second sample (identified as Run 32) has a starting level of dissolved carbon dioxide of about 12% and then decreased to about 6% in the early stages of the growth phase, followed with increasing level of dissolved carbon dioxide to a maximum of about 15%. The level of dissolved carbon dioxide then gradually went down to about 10% in the production phase. A third sample (identified as Run 40) has a starting level of dissolved carbon dioxide of about 6% to 10% during the lag phase and a high level of variability in dissolved carbon dioxide level ranging from about 5% to about 44% throughout days 4 through 11 of the cell culture process.

Figure 2A:
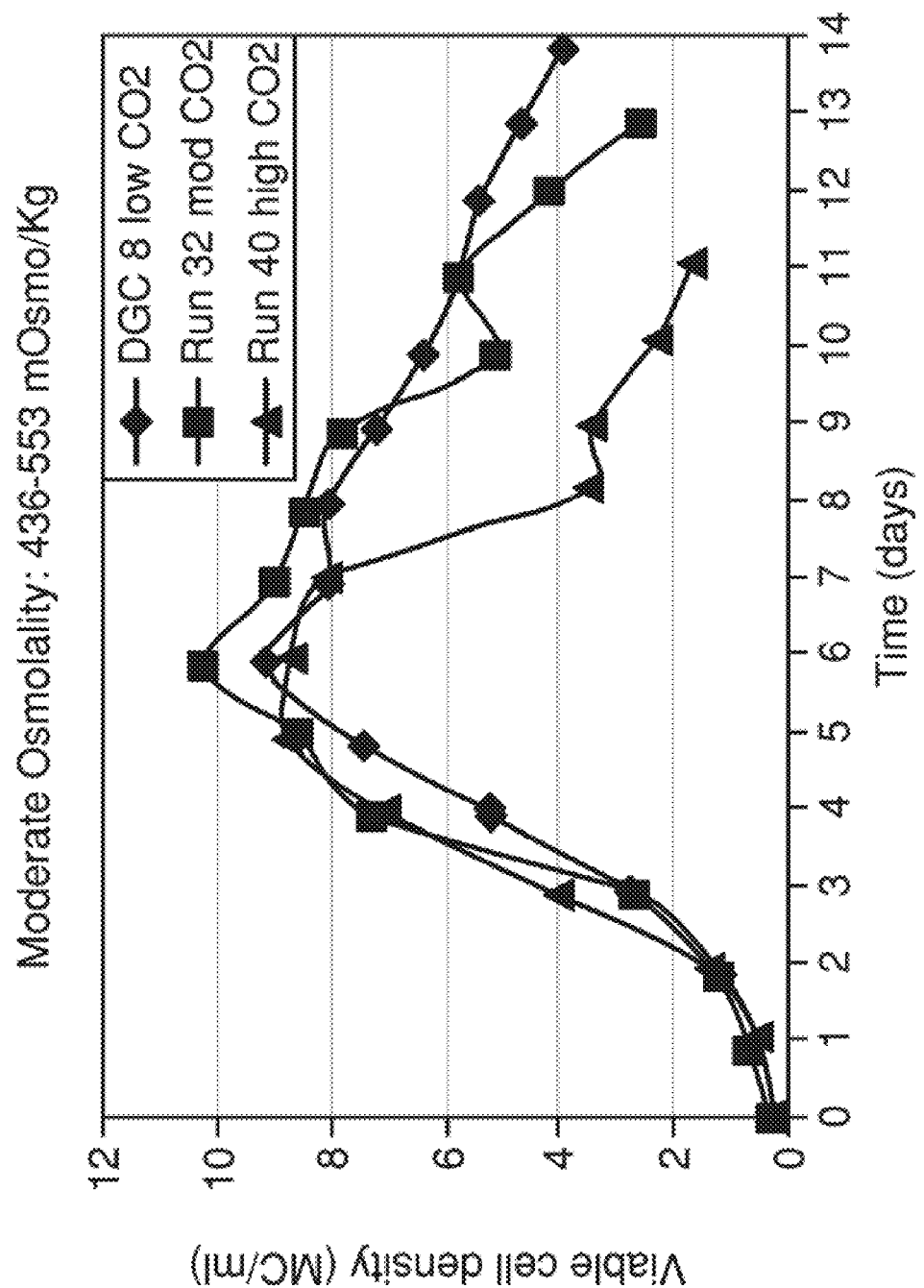
FIG. 2A is a graph that depicts viable cell density in a mammalian cell culture process as a function of time in days for the three different runs of a mammalian cell line in the process from FIG. 1 having a moderate osmolality.
Figure 2B:
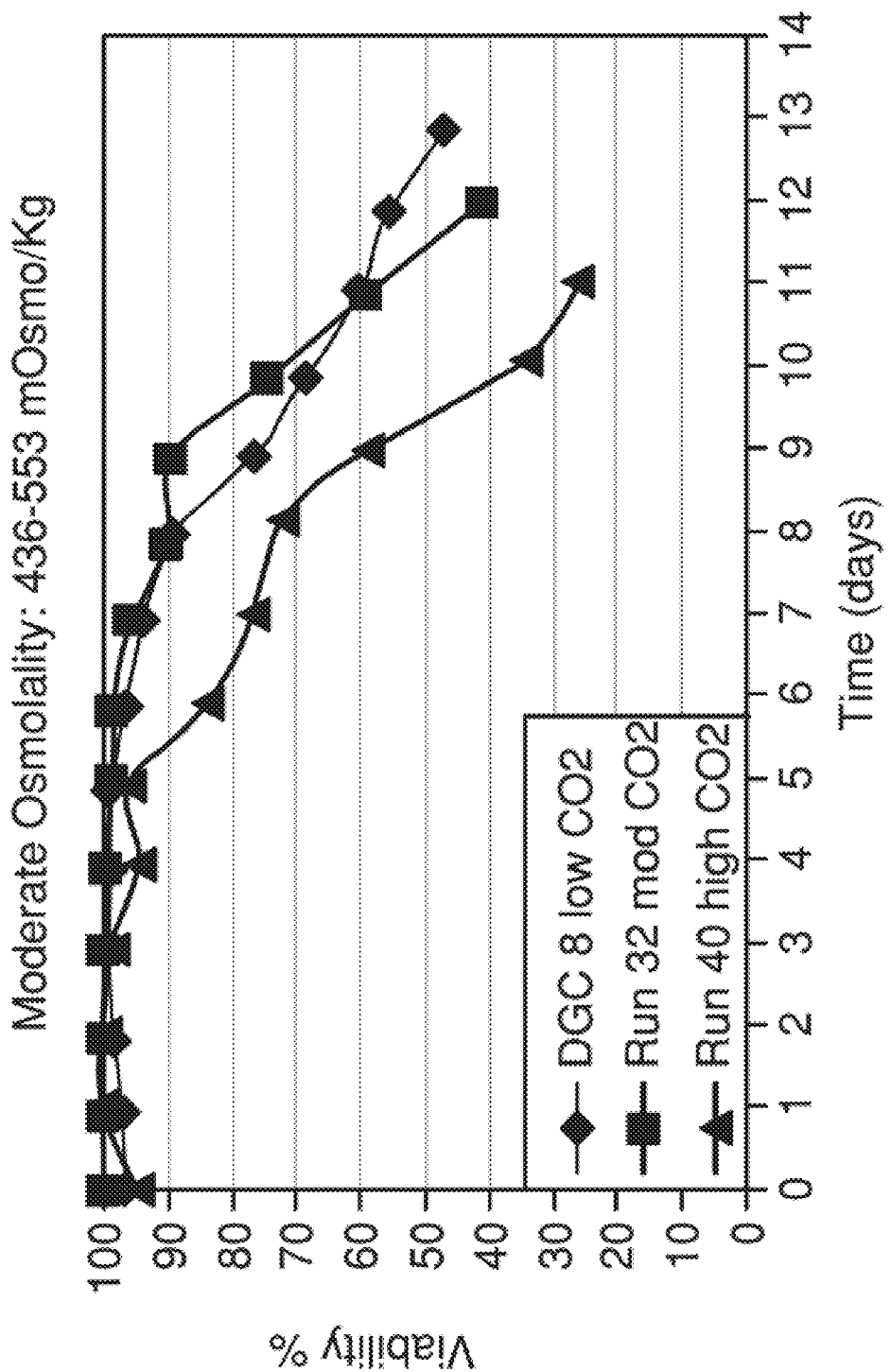
FIG. 2B is a graph that depicts cell viability as a percentage as a function of time in days for the three different runs of a mammalian cell line in the process from FIG. 1 having a moderate osmolality.
Figure 2C:
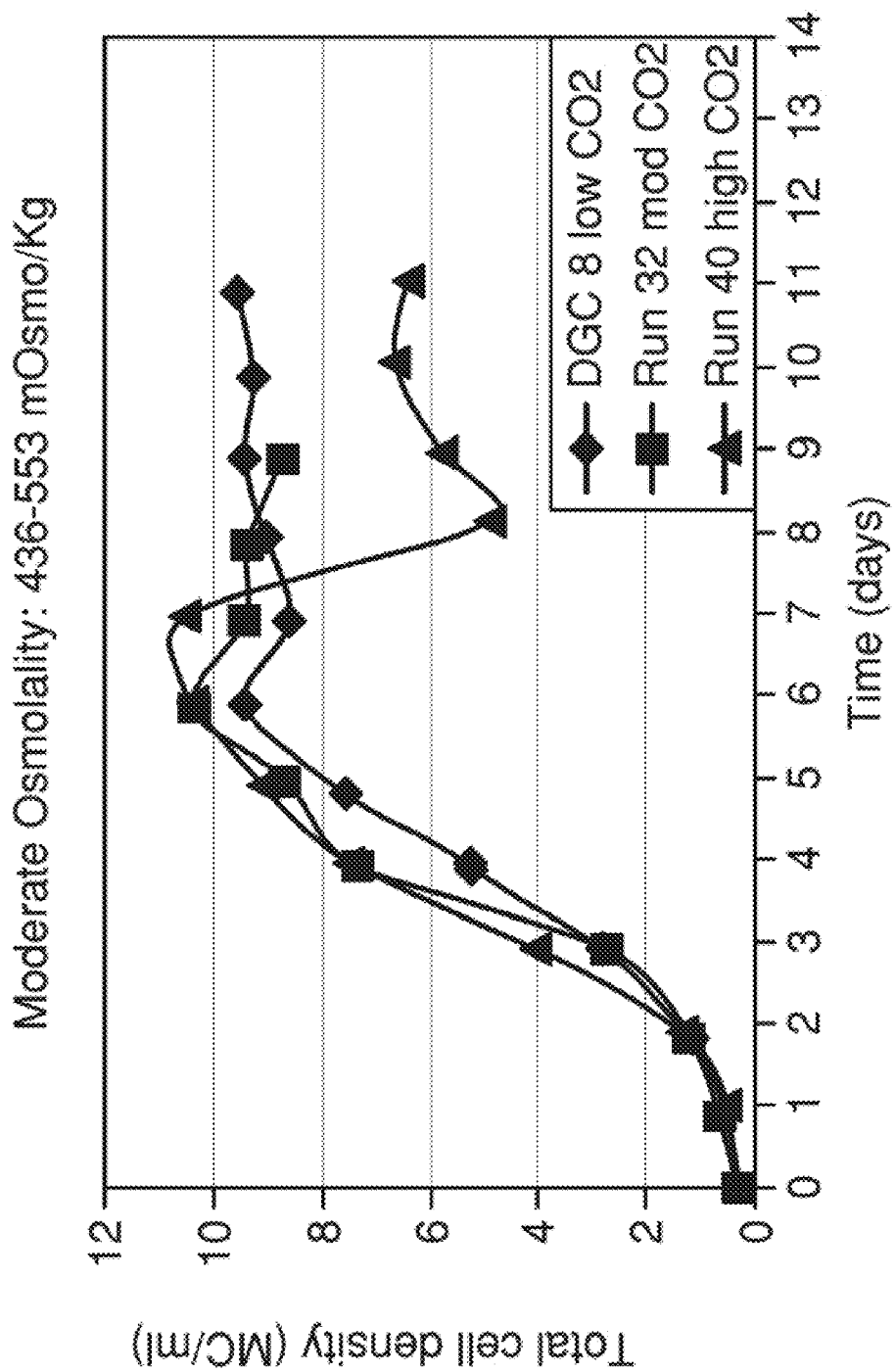
FIG. 2C is a graph that depicts total cell density cell in a mammalian cell culture process as a function of time in days for the three different runs of a mammalian cell line in the process from FIG. 1 having a moderate osmolality.

As seen in FIG. 2A DGC8 maintained a higher viable cell density (MC/ml) during the production phase of the mammalian cell culture process than Run 30 and a significantly higher viable cell density than Run 40. The data in FIGS. 2B and 2C depict similar graphs for baseline runs that when compared to FIG. 2A shows the benefits associated with the DGC technology disclosed in this application.

Figure 3A:
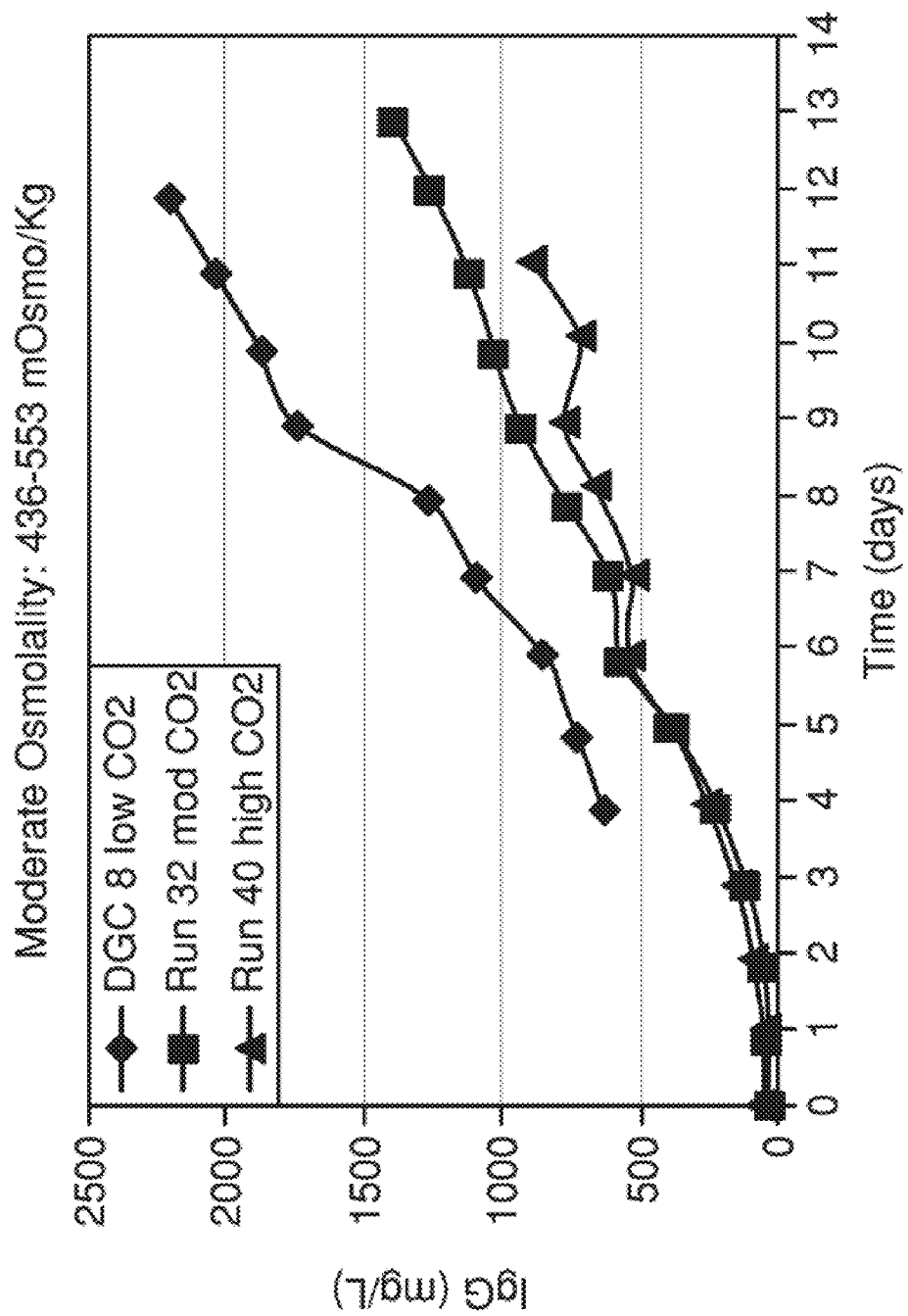
FIG. 3A is a graph that depicts biologic product concentration in a mammalian cell culture process as a function of time in days for the three different runs of a mammalian cell line in the process from FIG. 1 having a moderate osmolality.

Similarly, as seen in FIG. 3A, DGC8 maintained a higher product yield (mg/l) of IgG than the product yield of Run 30 and corresponding product yield of Run 40. Also, the specific productivity (pg/viable cell .day) in DGC8 with low $dCO_2$ was increased significantly. Specific productivity for the sample processes were about 40 pg/viable cell-day (DGC8), 20 pg/viable cell-day (Run 32) and 16 pg/viable cell-day (Run 40), respectively. As evidenced by the DGC8 data in FIGS. 1, 2A, 2B, 2C, and 3A, maintaining a stable and low level of dissolved carbon dioxide throughout the cell culture process can enhance cell viability, increase product yield and specific productivity.

FIGS. 3B and 3C show the measured osmolality levels in the DGC8 run as well as in Run 32. As expected the osmolality level increases substantially each time nutrients are added to the fed-batch mammalian cell culture process. However, when comparing the osmolality levels of FIGS. 3B and 3C, one observes a decrease or modulation in osmolality level a short time after the nutrient addition when the DGC process is used. Specifically, the starting osmolality level for run DGC8 was 370 mOsm/kg and thereafter ranges from between about 363 mOsm/kg to a maximum osmolality level of 475 mOsm/kg in the growth and production phases. The total rise in osmolality for this particular cell line was limited to about 112 mOsm/kg. On the other hand, the osmolality levels in Run 32 continue to rise throughout the growth phase and production phase of the cell culture process from a starting point of about 350 mOsm/kg to a maximum osmolality level of about 511 mOsm/kg which represents a rise of 161 mOsm/kg or about 35% more than run DGC8.

Figure 4:
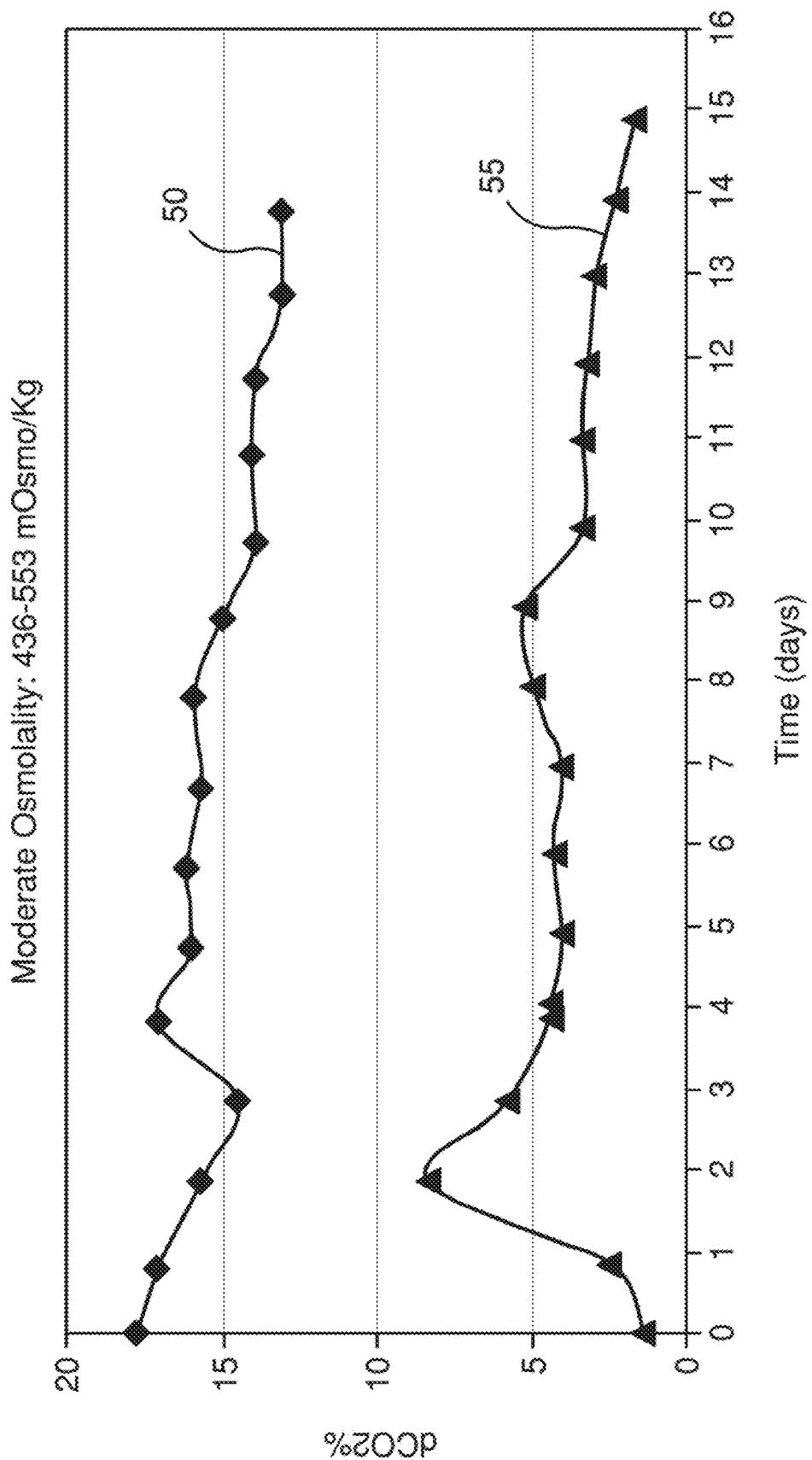
FIG. 4 is a graph that depicts percentage of dissolved carbon dioxide in a mammalian cell culture process as a function of time in days for two different runs of a mammalian cell line in a process having generally constant or stable osmolalities wherein the first run includes a low peak level of dissolved carbon dioxide and the second run includes a moderate overall peak level of dissolved carbon dioxide.
Figure 5:
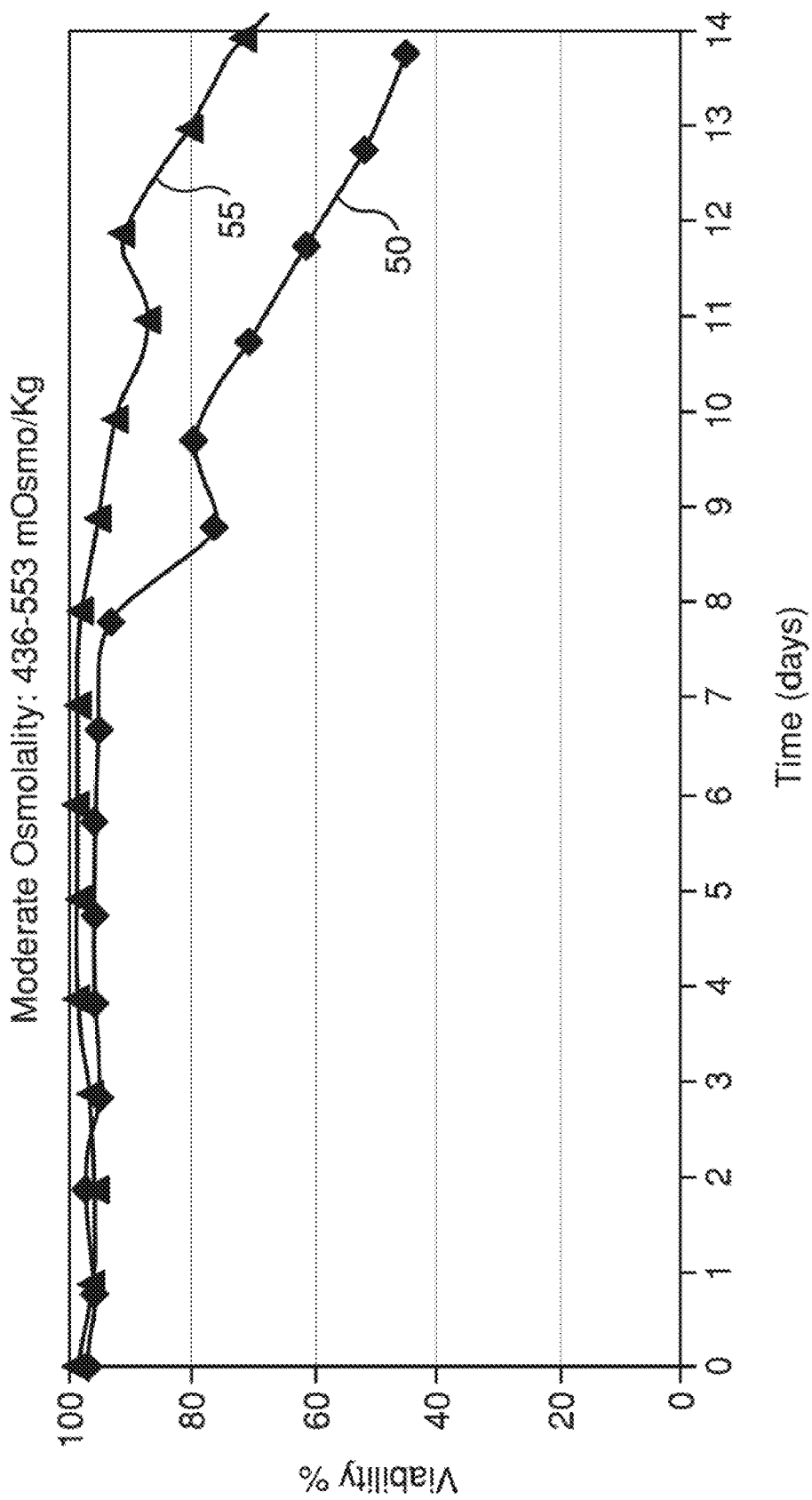
FIG. 5 is a graph that depicts viable cell density in a mammalian cell culture process as a function of time in days for the two different runs of a mammalian cell line in the process from FIG. 4 having a moderate osmolality and generally constant or stable levels of dissolved carbon dioxide.
Figure 6:
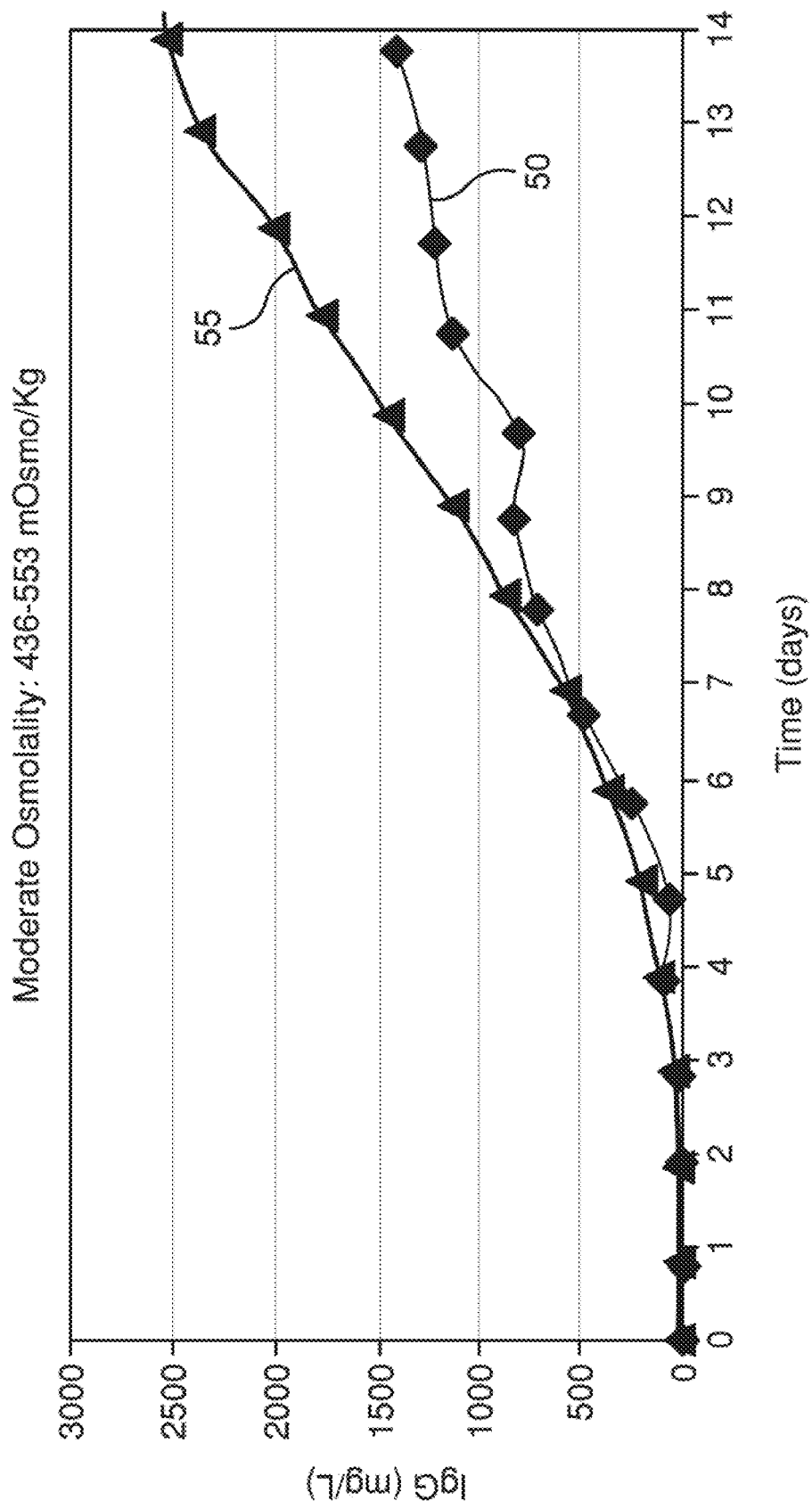
FIG. 6 is a graph that depicts biologic product titer or concentration in a mammalian cell culture process as a function of time in days for the two different runs of a mammalian cell line in the process from FIG. 4 having a moderate osmolality and generally constant or stable levels of dissolved carbon dioxide.

Referring now to FIGS. 4-6, there are shown graphs depicting the characteristics and results of two additional test runs of a mammalian cell culture process. As seen therein, the sample runs maintained a generally constant or stable level of dissolved carbon dioxide and moderate osmolality of the cell culture medium. Specifically, as shown in FIG. 4, Run 50 maintained a moderate level of dissolved carbon dioxide between about 13% and 18% during the exponential growth phase and production phase of the cell culture process whereas Run 55 maintained a low level of dissolved carbon dioxide between about 2% and 6% during the exponential growth phase and production phase of the cell culture process. As seen in FIG. 5 sample Run 55, with the generally stable but low level of dissolved carbon dioxide and moderate osmolality, demonstrated a higher percentage of cell viability during the production phase that Run 50 having a generally stable but moderate level of dissolved carbon dioxide and moderate osmolality. As seen in FIG. 6 sample Run 55, with the generally stable but low level of dissolved carbon dioxide and moderate osmolality, demonstrated a higher product yield during the production phase that Run 50 having a generally stable but moderate level of dissolved carbon dioxide and moderate osmolality. The results of these charts further confirm the conclusions drawn from FIGS. 1-3 that maintaining a stable and low level of dissolved carbon dioxide throughout the cell culture process enhances cell viability, increase product yield and specific productivity.

Impact of Dissolved Carbon Dioxide Levels in Mammalian Cell Culture

Refer back to FIG. 1, DGC8 shows a low $dCO_2$ level from the beginning of the run compared to the moderate $dCO_2$ level at the start of Run 32. At the peak of exponential cell growth phase, the $dCO_2$ of two runs were about the same at 5.7%. However, FIG. 3A shows that the protein product IgG produced during run DGC8 was almost twice as much as the protein product IgG produced during Run 32. This suggests that starting $dCO_2$ at the low levels and maintaining the same low $dCO_2$ levels until the production phase is also critical if one wishes to have an early harvest of IgG product. To generate a low starting $dCO_2$ level, it is necessary to calculate the chemical equilibrium $dCO_2$ level with the proper amount of sodium bicarbonate to be added to create a buffered solution at a pH of about 7.0. Of course, the surface gas exchange during the DGC process strips out any $CO_2$ generated during the exponential growth of the cell culture. After the start of the batch, the pH control is then switched to acid-base (e.g., hydrochloric acid-sodium hydroxide) system to avoid the necessary of adding any more $CO_2$ to maintain or reduce the pH level within the cell culture medium. Note that most cell culture processes do not switch from one buffer system to another during a batch cycle once the cell culture process has started.

Figure 7:
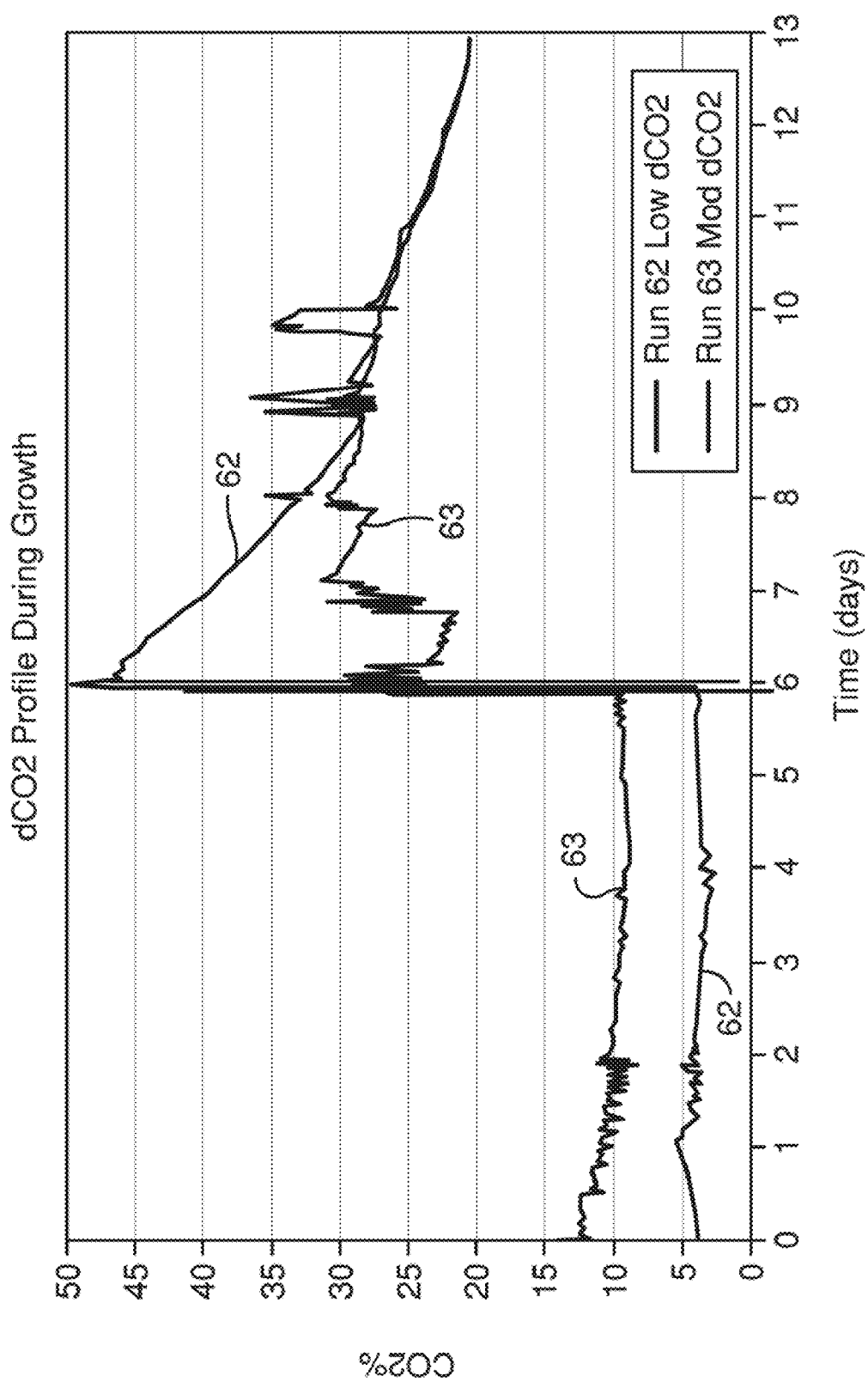
FIG. 7 is a graph that depicts the dissolved carbon dioxide profile during the growth and production phases of a mammalian cell culture process.

Turning now to FIGS. 7-11 there are shown sample data obtained from yet two additional mammalian cell culture process runs. FIG. 7 depicts the dissolved carbon dioxide levels during the growth and production phases of Run 62 which has a low level of dissolved carbon dioxide of about 5% during the lag and exponential growth phases and Run 63 which has a moderate level of dissolved carbon dioxide of about 10% during the lag and exponential growth phases of the cell culture process. In both Run 62 and Run 63, the dissolved carbon dioxide levels were artificially raised to an average of 30% after day 6 when the cell culture process enters the production phases. Gas flow rate to the headspace and agitation speed were reduced to lower the stripping rate, while additional carbon dioxide gas was added to the headspace. The purpose of Run 62 and Run 63 was to examine the impact of dissolved carbon dioxide on the cells during the production phase only. Lower cell viability and protein product IgG yield were expected from both Run 62 and Run 63 compared to Run DGC8 where dissolved carbon dioxide levels were precisely controlled throughout the cell culture process.

Figure 8:
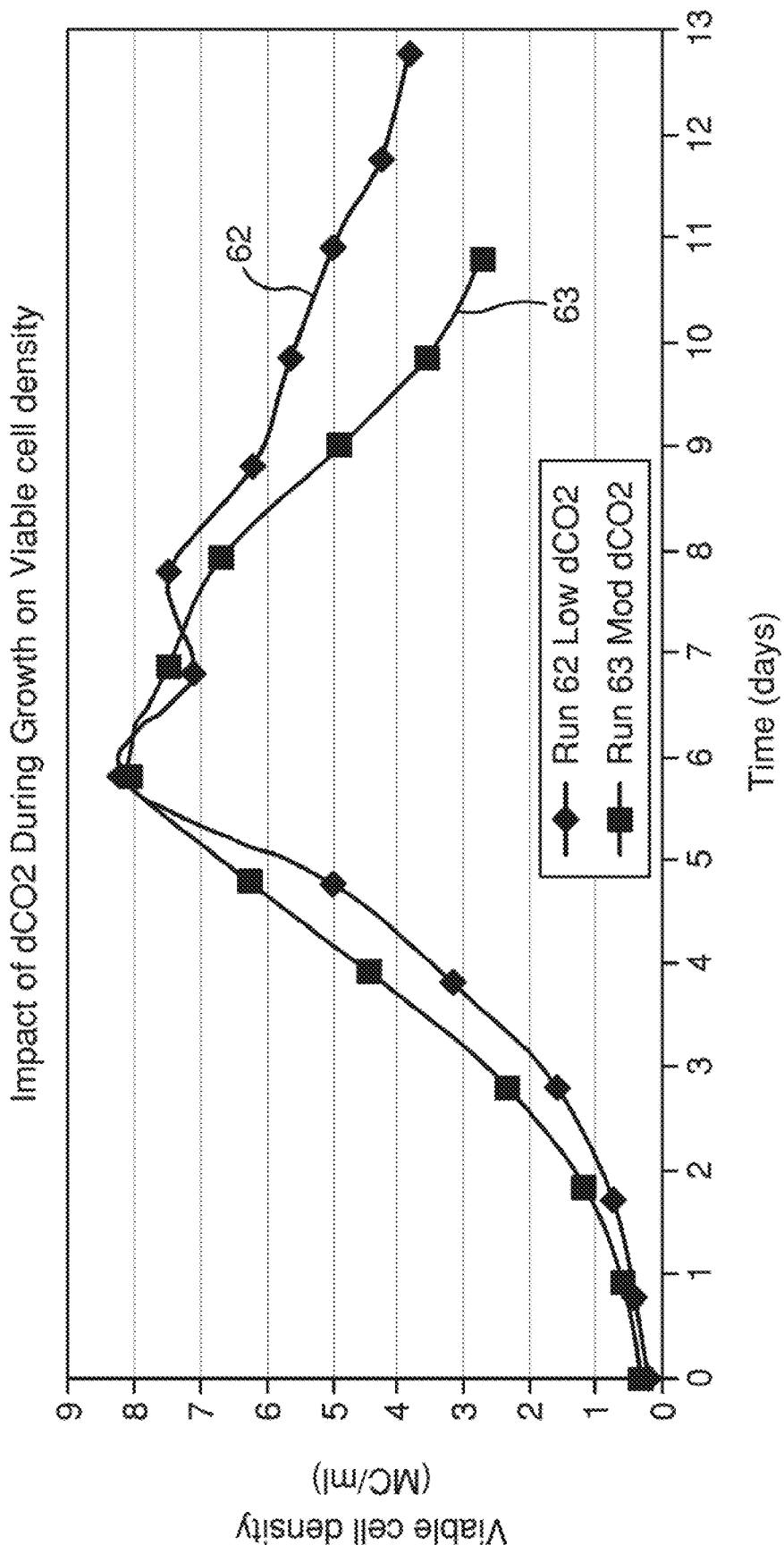
FIG. 8 is a graph that depicts viable cell density in a mammalian cell culture process as a function of time in days for yet another two different runs of a mammalian cell line in which different but generally constant levels of dissolved carbon dioxide are maintained.
Figure 10:
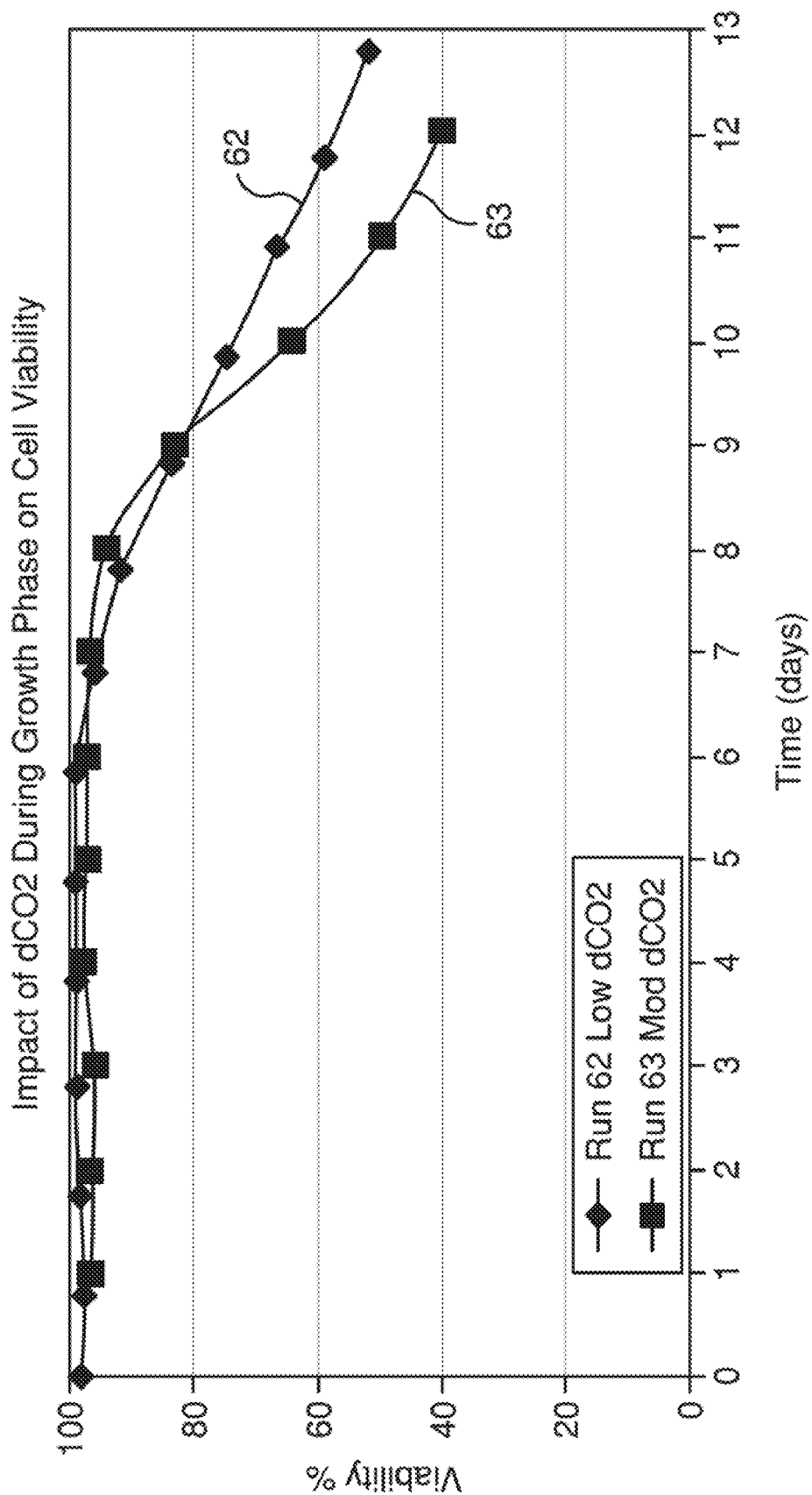
FIG. 10 is a graph that depicts percentage of viable cells in a mammalian cell culture process as a function of time in days for the two different runs of the mammalian cell line in the process from FIG. 8 having different but generally constant levels of dissolved carbon dioxide.

FIG. 8 and FIG. 10 show that the viable cell density and % cell viability for both Run 62 and Run 63 were about the same during the growth phase. However, Run 62, with the low level of dissolved carbon dioxide during the growth phase demonstrated a higher degree of cell viability during the production phase than Run 63 which had a moderate level of dissolved carbon dioxide during the growth phase. Therefore, the cells in Run 62 were exposed to lower levels of dissolved carbon dioxide during the growth phase and were healthier than cells in Run 63 exposed to higher levels of dissolved carbon dioxide during the growth phase.

Figure 11:
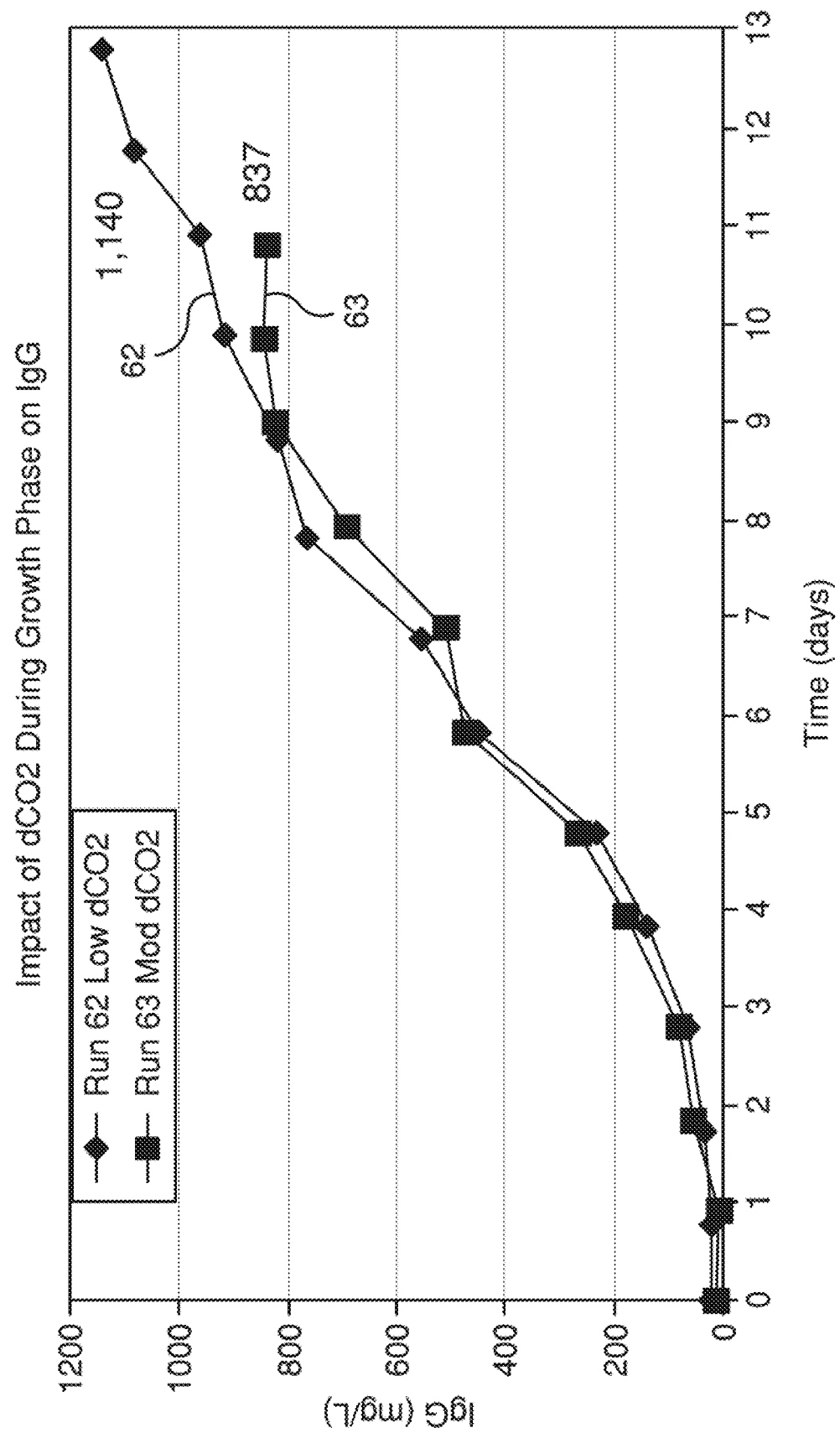
FIG. 11 is a graph that depicts biologic product yield or titer in a mammalian cell culture process as a function of time in days for the two different runs of a mammalian cell line in the process from FIG. 8 having different but generally constant levels of dissolved carbon dioxide.
Figure 12:
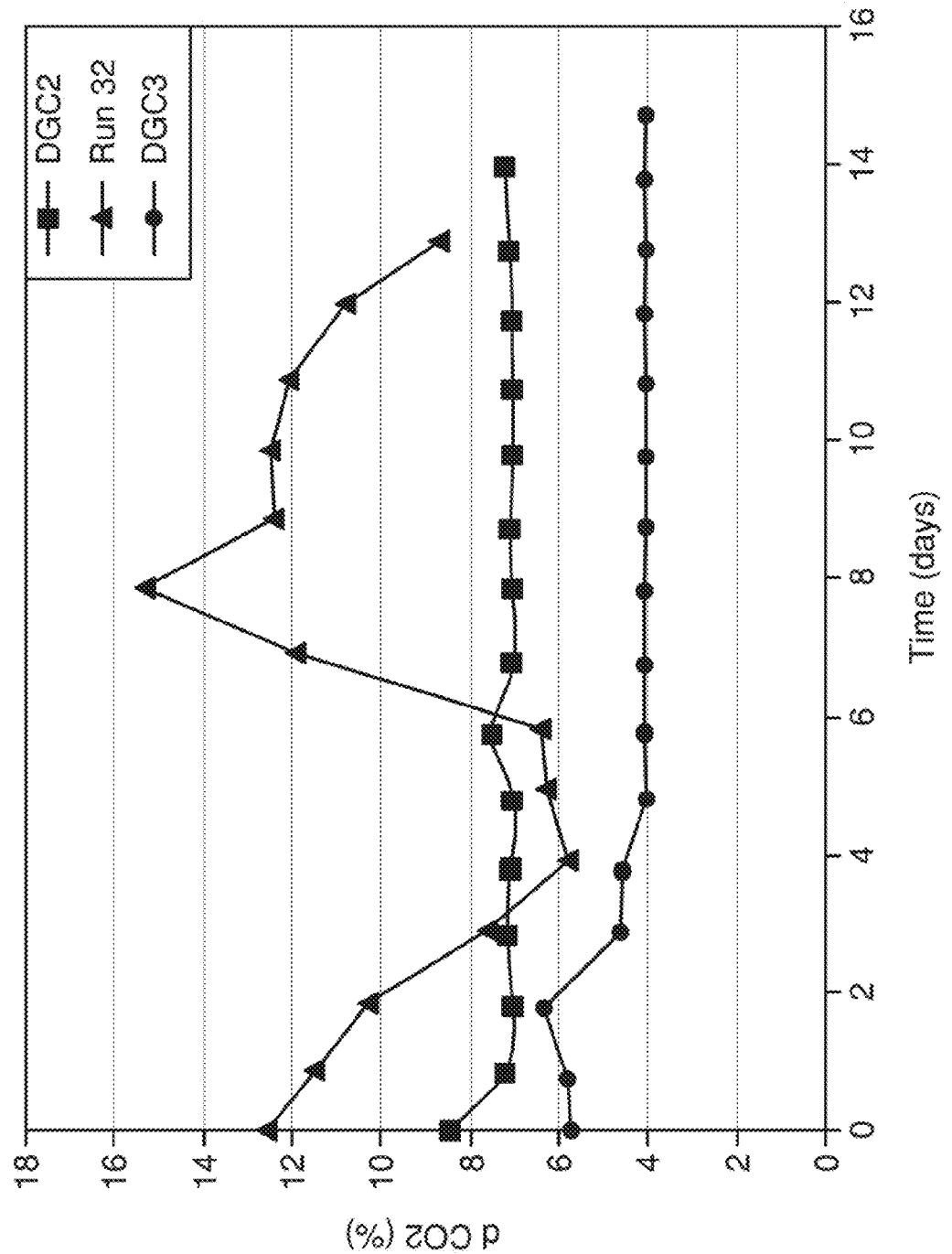
FIG. 12 is a graph that depicts dissolved carbon dioxide in a mammalian cell culture process as a function of time in days for the two different runs using the present Dynamic Gas Control (DGC) process compared against a standard run.
Figure 13:
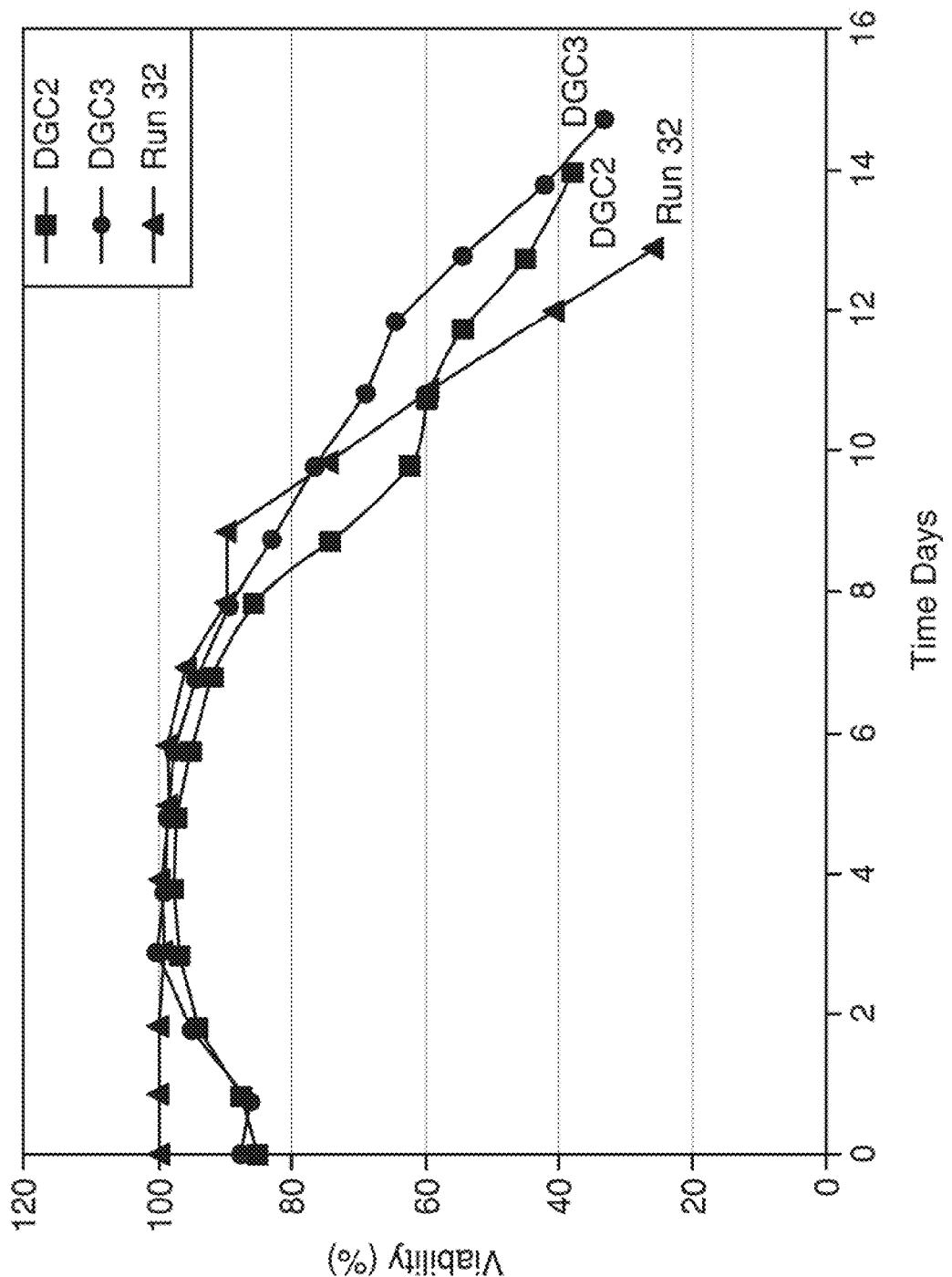
FIG. 13 is a graph that depicts cell viability in a mammalian cell culture process as a function of time in days for the two different runs using the present Dynamic Gas Control (DGC) process compared against a standard run.
Figure 14:
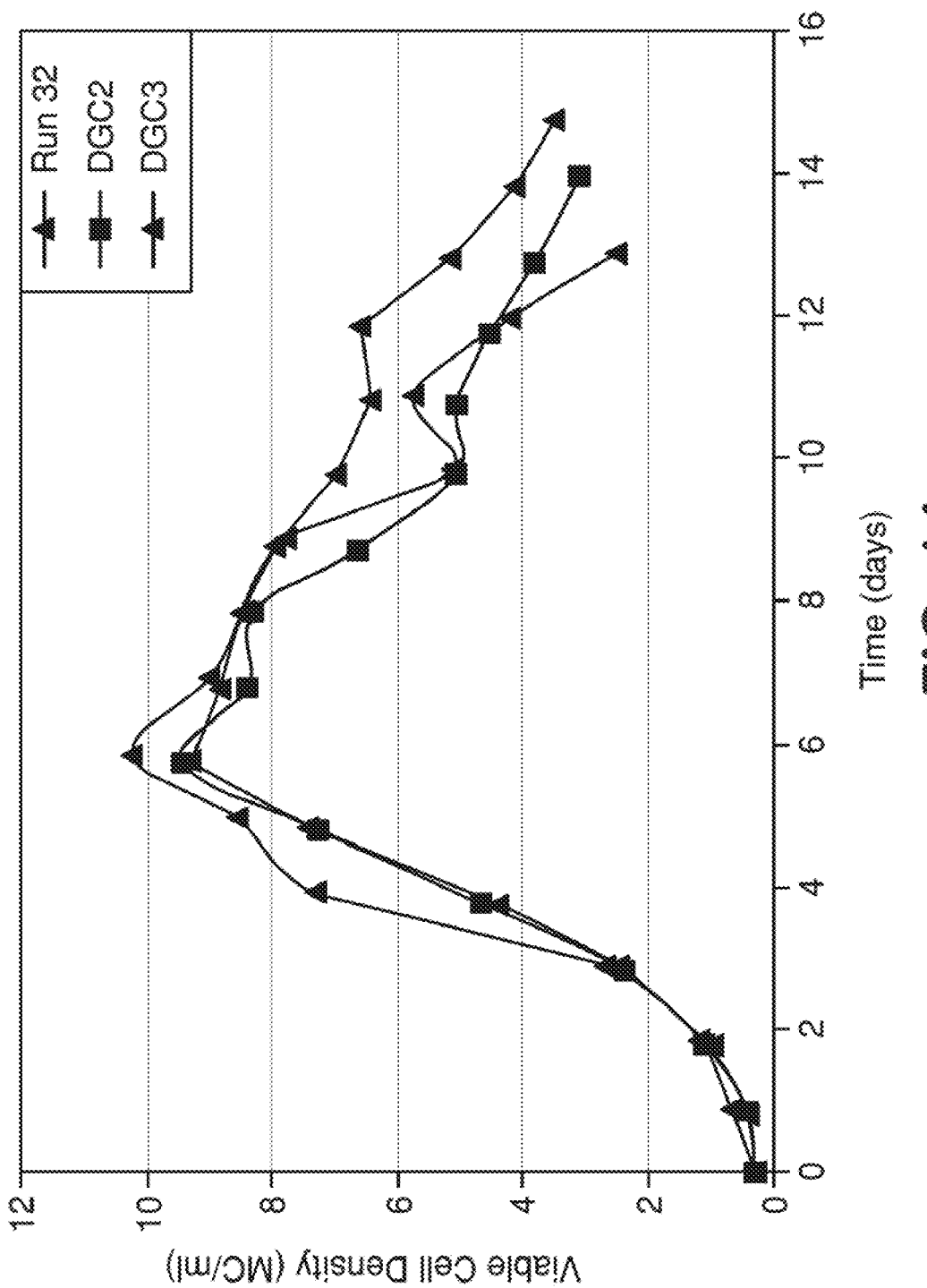
FIG. 14 is a graph that depicts viable cell density in a mammalian cell culture process as a function of time in days for the two different runs using the present Dynamic Gas Control (DGC) process compared against a standard run.
Figure 15:
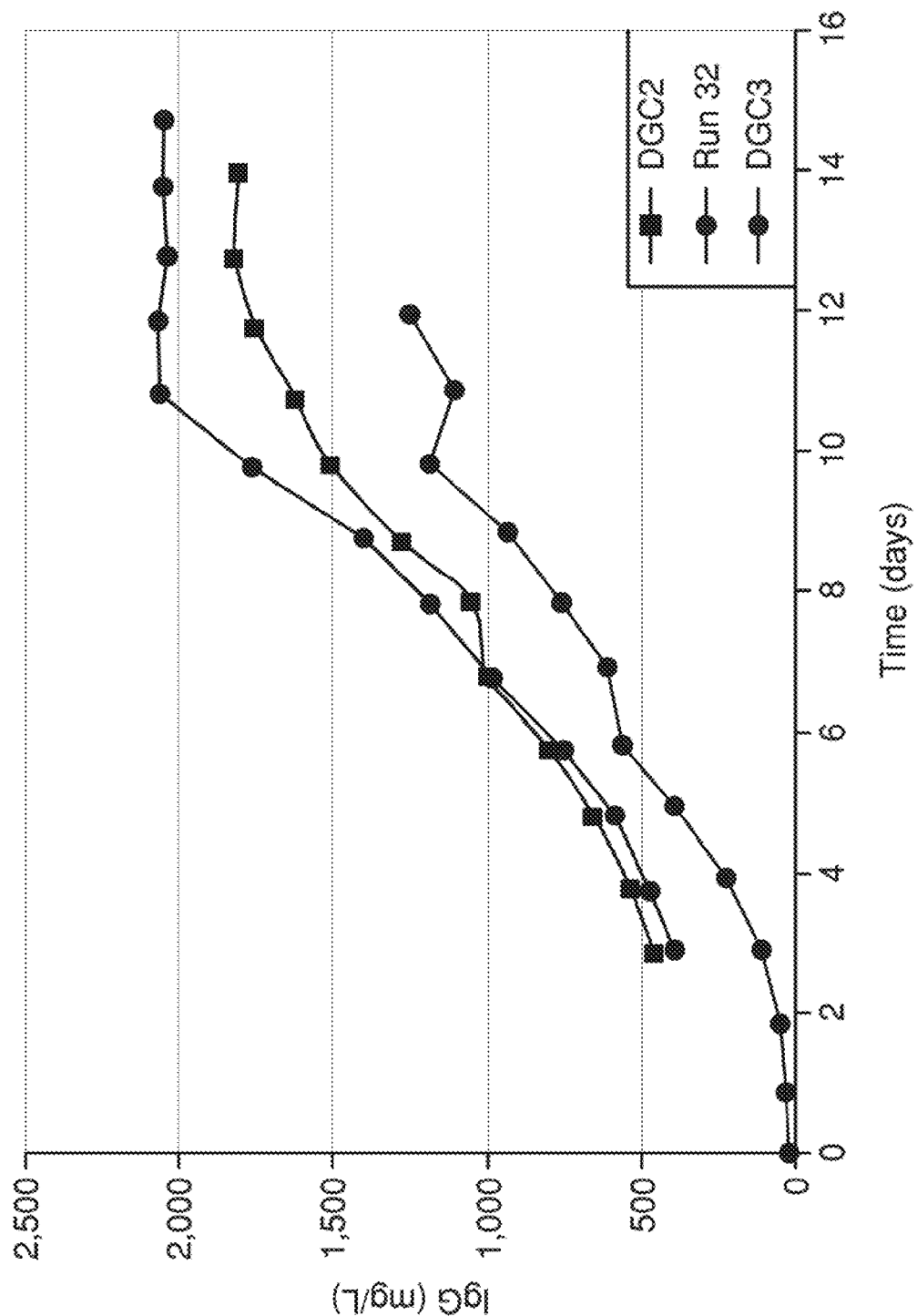
FIG. 15 is a graph that depicts biologic product yield or titer in a mammalian cell culture process as a function of time in days for the two different runs using the present Dynamic Gas Control (DGC) process compared against a standard run.

FIG. 11 shows that sample Run 62, with the starting low level of dissolved carbon dioxide also demonstrated a higher IgG product yield of 1,140 mg/L during the production phase than Run 63 having a moderate level of dissolved carbon dioxide with IgG product yield of 837 mg/L. Run 62 could have been done even better if the dissolved carbon dioxide level had not been spiked excessively to 45%. These two runs suggest that dissolved carbon dioxide has an impact on the IgG protein product yield from the cell culture process. Comparing Run 62 and Run 63 to DGC8 shown in FIG. 3 where no spike of dissolve carbon dioxide level was introduced during the production phase, the IgG protein product yield of DGC8 is more than double that of Run 62 which suffered from the high dissolved carbon dioxide level during the production phase. Clearly, the impact of dissolved carbon dioxide levels in the growth phase and/or production phase have different effects on the cell viability and product yield.

Optimization of Dissolved Carbon Dioxide Levels and Osmolality

The presently disclosed system and methods preferably maintain a generally constant or stable level of dissolved carbon dioxide of less than 10% during the lag and exponential growth phases, and more preferably around 3% to 5% while maintaining a moderate level osmolality of between about 300 and 560 mOsmo/kg, and more preferably between about 400 and 500 mOsmo/kg during the lag phase and exponential growth phase (See FIGS. 1 and 4). This combined dissolved carbon dioxide level and osmolality process condition provides longer cell viability and highest biological product yield during the production phase for selected mammalian cell culture processes (see FIGS. 2, 3, 5 and 6).

In batch cell culture processes, the change in osmolality is relatively small. Similar to the chemical equilibrium calculation of starting dissolved carbon dioxide, the starting osmolality should be calculated from all the components in the starting medium solution. In conventional batch process, osmolality will increase when carbon dioxide is generated from the metabolizing cell mass and sodium bicarbonate has to be added to rebalance pH.

For a fed-batch process, osmolality will also show step changes as nutrients are added in intermittent step to prolong growth and production. As discussed earlier, each g-mole of salt or electrolyte will dissociate into two g-moles of osmolality. Each g-mole of glucose, glutamate and other organic nutrients will contribute one g-mole to the total osmolality. FIG. 6A shows the osmolality profile of DGC8 as a typical profile of a good culture run with the present Dynamic Gas Control (DGC) process technology. The large step increases are due to the time of nutrient additions. After each of the nutrient addition, the osmolality actually decreased as glucose and glutamate were being consumed. In the popular fed-batch processes, however, osmolality will take a bigger step increase every time additional nutrient is added into the broth at selected times during the cell culture process cycle. Depending on the pH and operating conditions, glucose being consumed may be converted into lactates, resulting in no net changes in system osmolality. However, glucose can also be converted directly into carbon dioxide gas and water. If the carbon dioxide gas is stripped effectively as with present DGC process technology, a temporary decrease in osmolality is observed. Otherwise, the osmolality levels in the cell culture medium continue to increase due to the addition of alkaline or bicarbonates necessary to neutralize the pH depressed by dissolved carbon dioxide.

As shown in FIG. 6A, DGC8 clearly demonstrated the ability of the present invention to reduce or maintain the osmolality after each nutrient addition during the fed-batch cycle. By keeping the osmolality level within a minimum or preferred range, additional salts and/or nutrients can be added to manipulate the osmolality levels to the desirable optimum profile or range. Since mammalian cells require certain electrolytes and nutrient to survive and thieve so the optimum osmolality level is not necessary the lowest osmolality. However, without continuous contributions from the pH adjustment due to excess dissolved carbon dioxide, optimization of osmolality level is possible.

To control the cell culture process at the most desirable osmolality range requires not only the starting osmolality level to be pre-determined by calculations or experiments, but the osmolality level at each of the nutrient and/or media addition is needed to be taken in account, so that final osmolality level can fall into the desired range. As discussed above, having an efficient dissolved carbon dioxide removal or stripping process to remove the accumulating carbon dioxide also has an effect on the osmolality level. By controlling both the dissolved carbon dioxide and osmolality at the desirable levels, significant product yield and product purity improvements can be realized.

Figure 9:
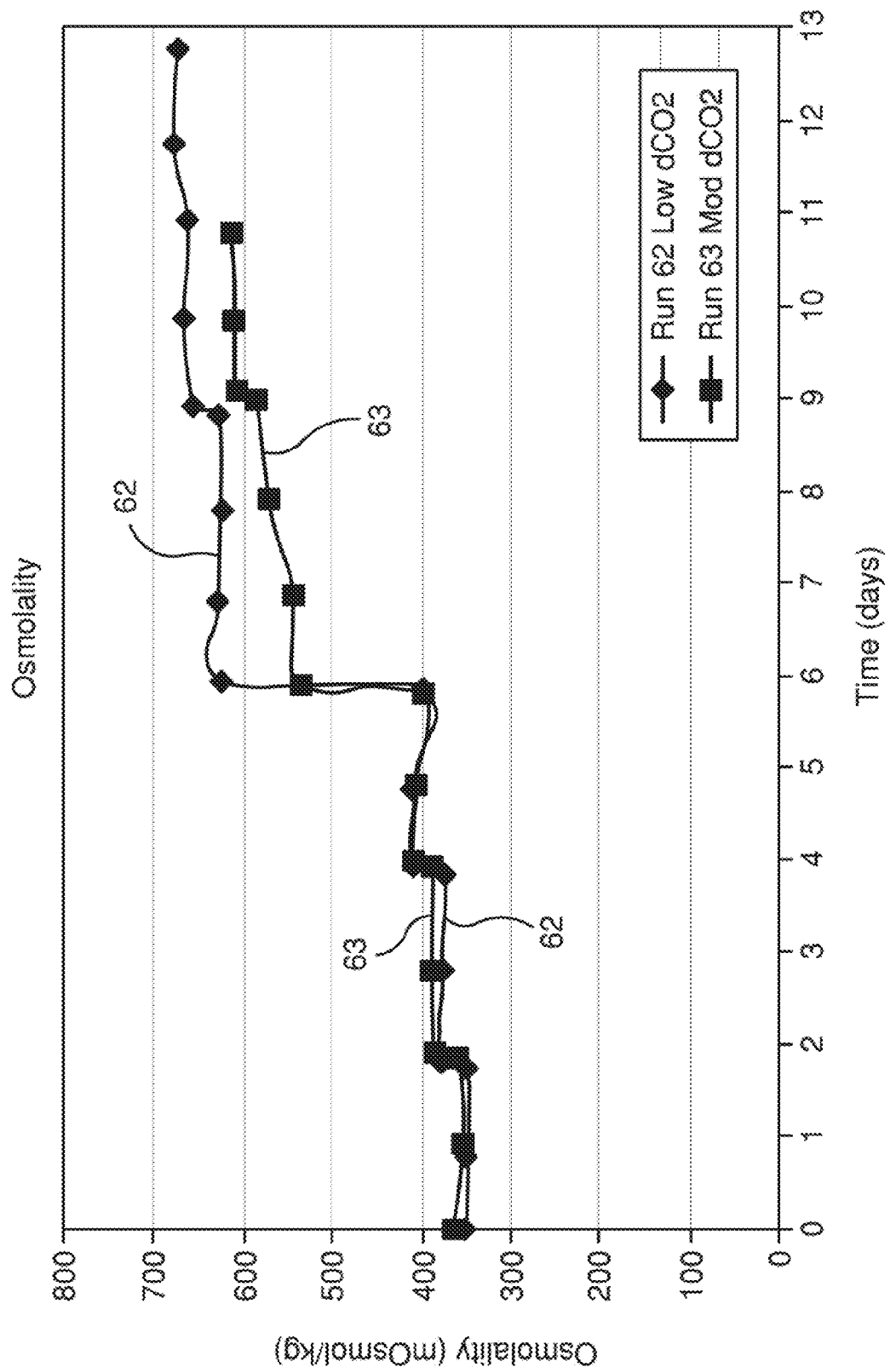
FIG. 9 is a graph that depicts osmolality in a mammalian cell culture process as a function of time in days for the two different runs of the mammalian cell line in the process from FIG. 8 having different but generally constant levels of dissolved carbon dioxide.

FIGS. 7 and 9 show the effects of high dissolved carbon dioxide on increasing osmolality and reducing product yield. During the entire growth phase for Run 62 and Run 63, the dissolved carbon dioxide at the 5% to 10% range did not have large impact on the osmolality level of either runs. The increases of osmolality level from about 350 mOsmo/kg to about 400 mOsmo/Kg were largely contributed by the media and nutrient addition. At the beginning of the production phase, the dissolved carbon dioxide concentration was allowed to rise with the $dCO_2$ stripping rate reduced. As shown the FIG. 9, the osmolality level increased drastically with the sodium bicarbonate automatically injected by pH controller due to the presence of excess carbon dioxide produced by the cells. In contrast to osmolality levels of run DGC8 shown in FIG. 6A, the osmolality level of Run 63 continued to increase to about 600 mOsmo/kg while Run 62 with higher peak dissolved carbon dioxide increased even further to about 680 mOsmo/kg. With high dissolved carbon dioxide concentrations at production phase and uncontrolled osmolality, both Run 62 and Run 63 have much lower IgG product yield (1,140 mg/L and 837 mg/L respectively) than the fully controlled DGC8 (2,300 mg/L) using Dynamic Gas Control process.

Turning now to FIGS. 12 through 17, there are shown charts containing data comparing the cell culture process using Dynamic Gas Control (DGC) process compared to a cell culture process without employing the Dynamic Gas Control (DGC) process. The data on the illustrated charts suggest that sample runs employing the Dynamic Gas Control (DGC) process at moderate osmolality, namely samples DGC2 and DGC3, provide much higher product yield than process without the DGC control (e.g. Run 32).

In sample process DGC2, the dissolved carbon dioxide was started at about 8.45%, and was subsequently maintained in a range between about 7.0% to 7.5% throughout the remaining cell culture process. In sample process DGC3, the dissolved carbon dioxide was started at about 5.5%, and was maintained in a range between about 5.5% to 6.3% for Day 1 and Day 2, and subsequently decreased to about 4.5% at Day 3 and Day 4, and further reduced to about 4.0% from Day 4 to Day 15. Finally, Run 32: had a dissolved carbon dioxide profile very typical cell culture process where the average $dCO_2$ was maintained about 6% in the growth phase, followed with increasing $dCO_2$ to about 15%, then gradually lowered to about 10% in the production phase.

The data contained in FIGS. 12-17 shown that the dissolved carbon dioxide levels can be well maintained at desired low level through the process with Dynamic Gas Control (DGC) process. Both the DGC2 and DGC3 sample runs had higher viable cell density and viability during later stages of protein production. Sample run DGC3, with the lowest controlled dissolved carbon dioxide level, had the highest product titer among these three runs, and reached maximum product titer much earlier than either DGC2 or Run 32.

Method of Shortening Batch Time with Improving Product Purity

During the production phase, the cells are dying off as the nutrients are running out and other byproducts and wastes such as ammonia and lactate are reaching toxic levels. Simple replacement of glucose with sucrose, for example, may delay the onset of the toxic levels and resulting inducement of cell death by reducing lactate production. Delaying the onset of cell death improves the overall cell viabilities and allows for higher product yields. Eventually, the cells will die. Dead cells typically decompose and release proteases and other undesirable enzymes. These proteases can destroy the live cells and even degrade the protein products that were already formed. Mammalian cell culture processes that produce recombination proteins are especially sensitive to the proteases released from the dead cells. Therefore, processes producing recombination proteins are normally cut short before cell viabilities drop significantly below 90%.

Turning again to FIG. 13 and FIG. 15, Run 32 represents a well operated conventional mammalian cell culture process that does not facilitate surface gas exchange at the top surface of the cell culture medium in the bioreactor. The batch associated with Run 32 ran for 12 days until the cell viability dropped below 40%. At harvest time, the product yield was 1,250 mg/L. In order to harvest Run 32 at the desired 90% cell viability, the batch time would have to be shortened to 7 days and the product yield would be only 650 mg/L of product. In contrast, DGC3 using the present Dynamic Gas Control process including surface gas exchange started producing products much earlier on even during the growth phase. DGC3 would have yielded 2,060 mg/L of products if the batch was to harvest in 12 days with 66% cell viability. To harvest DGC at 90% cell viability and 7 days, the yield would be reduced to 1,050 mg/L of product. From a biopharmaceutical point of view, shorten processing time with higher product purity may provide significant competitive advantages for some cell lines. Therefore, using the Dynamic Gas Control process disclosed herein would allow biopharmaceutical producers the choice of either shorten the cell culture process cycle to make high purity products or increase substantially the yield of protein products when compared to conventional cell culture processes at the equivalent batch time and same nutrient content.

Optimization of the Dynamic Gas Control (DGC) Process

Figure 16:
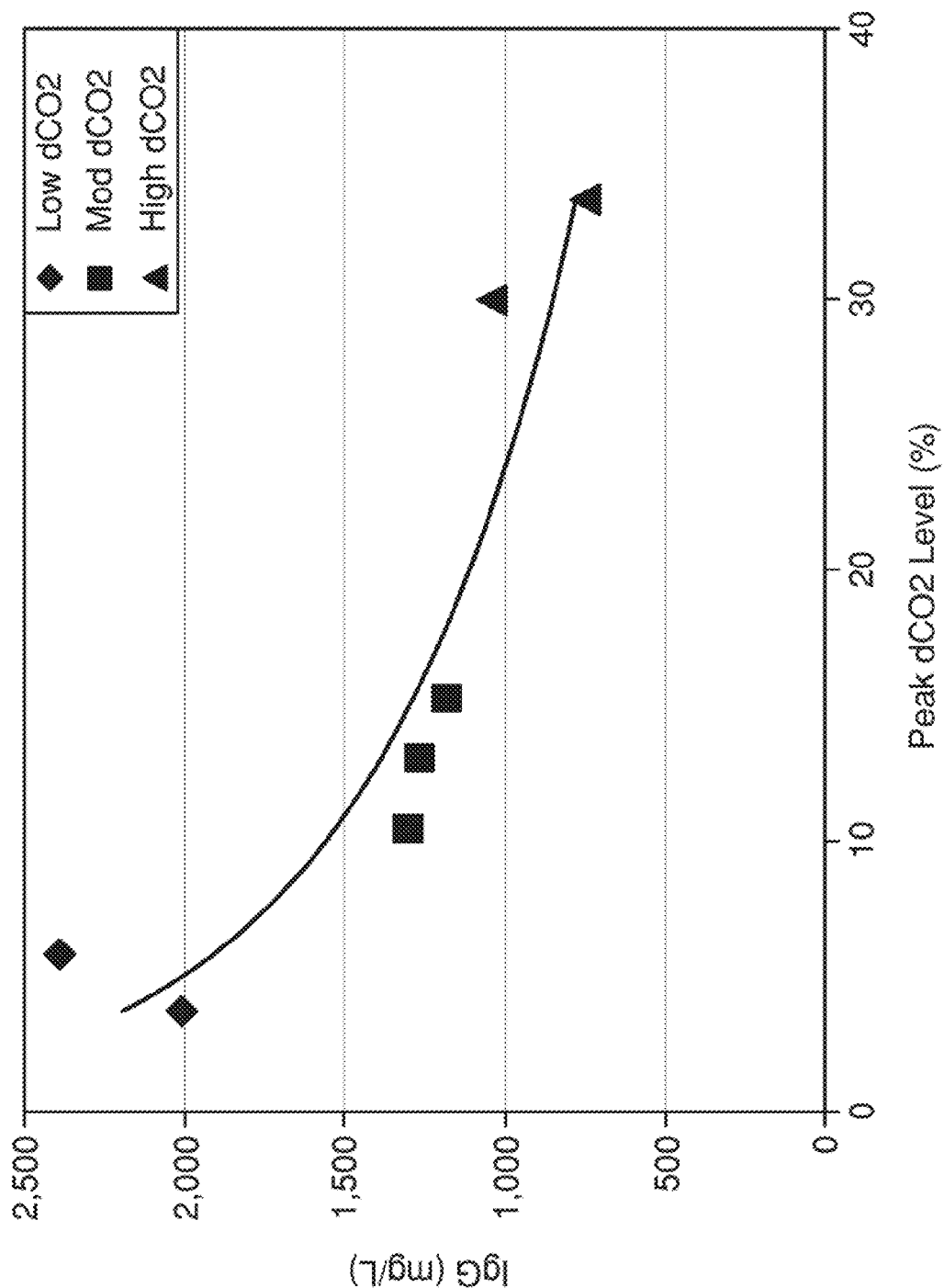
FIG. 16 is a chart that depicts the trend of IgG titer versus peaked $dCO_2$ in the cell culture process with varying levels of osmolality.
Figure 17:
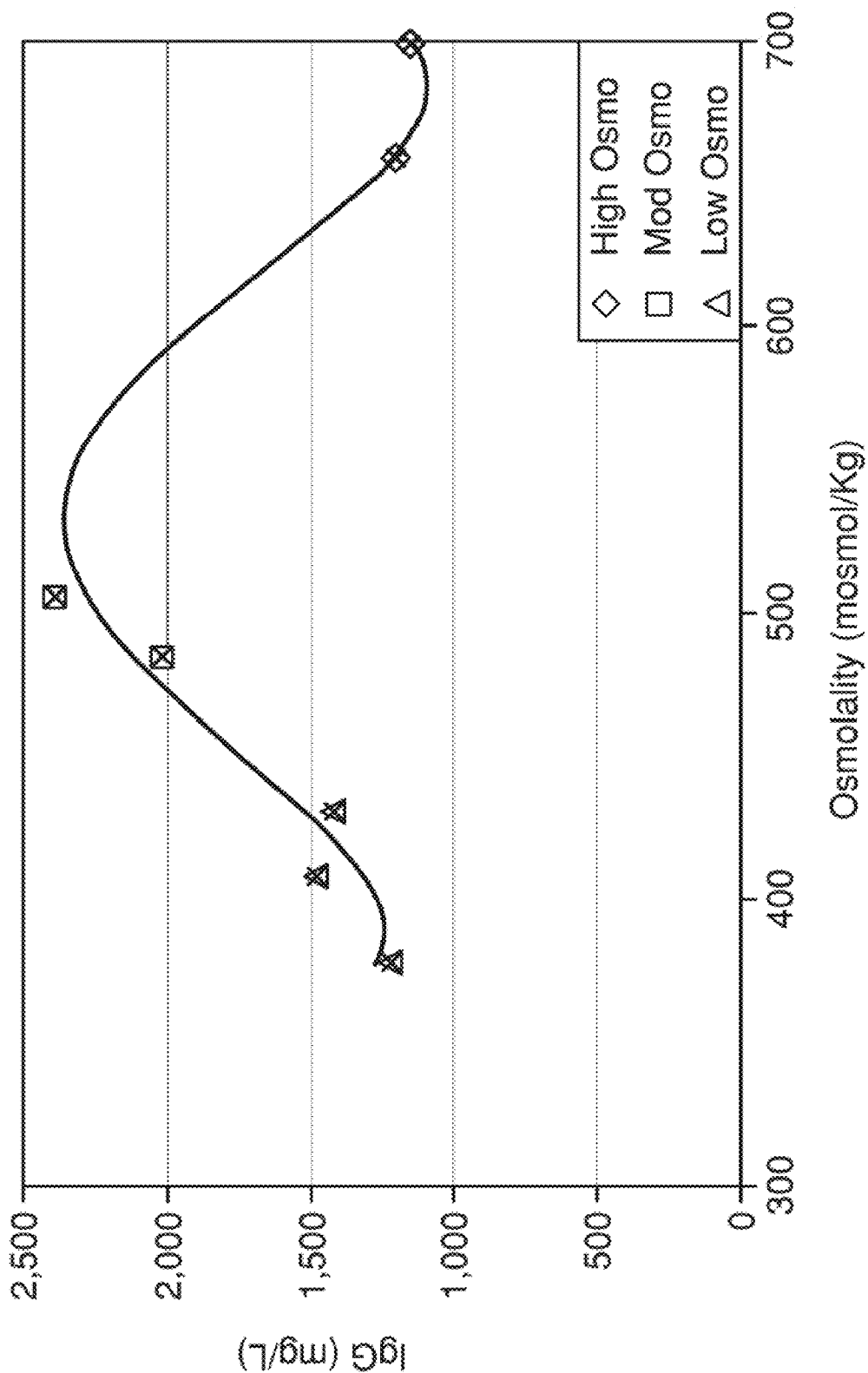
FIG. 17 is a chart that depicts the trend of IgG titer versus maximum osmolality in the DGC type cell culture process with low levels of dissolved carbon dioxide.

FIG. 18 is a table that provides the cell culture process data collected during various sample runs at various combinations of osmolality and peak dissolved carbon dioxide. FIG. 16 is a plot of selected data from the table with various peak carbon dioxide level but only moderate osmolality. As seen therein, the lowest peak dissolved carbon dioxide levels of about 5% or less provide the highest product yield. Note that the physiological carbon dioxide in human blood stream is also about 5-6%. FIG. 17 is a plot of another set of data with various osmolality levels but only moderately peak dissolved carbon dioxide levels. FIG. 17 illustrates that an optimum maximum osmolality level exists at around 500 m Osmo/kg for this particular cell line.

The present DGC system and method also provides for maintaining a low level of dissolved carbon dioxide of less than 10%, and more preferably around 5% or less while diluting the mammalian cell culture batch with water during the production phase while also adding selected amounts of additional nutrient during the production phase. This dilution and nutrient supplementation procedure provides higher mammalian cell culture bioreactor product yields and also appears to dilute some of the critical toxic waste buildup.

All three of the above process optimization techniques, alone or in combination, enhance typical mammalian cell culture bioreactor product purity and product yields by controlling a plurality of critical process parameters, including the level of dissolved carbon dioxide and osmolality in addition to the previously recognized process parameters of pH, dissolved oxygen level, temperature, pressure, nutrient and waste product profiles in the media, agitation, gas sparging, nutrient feed and product harvest.

The impact of the above-identified parameters on the process yields are initially established either under scaled-down conditions in a smaller scale bioreactor or at full commercial bioreactor scale for a given cell line. After establishing the optimal levels or ranges of dissolved carbon dioxide, osmolality, pH, dissolved oxygen, temperature as well as nutrient and product levels in the cell culture media suitable for commercial production, the DGC process allows tight control of the agitation profile and gas flow in the headspace to achieve these optimal conditions.

Broadly described, the present optimization and control method comprises: (a) process optimization phase; and (b) active control phase. The process optimization phase involves empirically determining the desired pH osmolality and dissolved carbon dioxide levels for a given mammalian cell culture process, cell line and bioreactor configuration. Based on the targeted starting osmolality level and dissolved carbon dioxide level, the bioreactor media is prepared with the proper amount of bicarbonate as buffer. This initially prepared media will have pH generally on the alkaline side. The pH of the solution is adjusted to the desired level by introducing carbon dioxide gases during start-up or preparation of the cell culture media. Once the desired pH level is reached, the carbon dioxide gas is turned off for the remaining portion of the cell culture process cycle and pH control is switched to acid-base type pH control system. When Dynamic Gas Control process is used, however, the addition of acid or base to control the pH is rarely needed.

The active control phase uses a microprocessor-based controller to establish the initial settings as well as permissible values or ranges for overlay gas composition, overlay gas flow rate, pH (acid addition, base addition), nutrient addition, etc. to achieve the desired dissolved carbon dioxide and osmolality in the bioreactor while maintaining pH within the desired set points and maintaining one or more of the other process parameters such as dissolved oxygen level, agitator speed, temperature, pressure, nutrient content, waste product content, etc. within specifications. Individual gases or gas mixtures relevant for cell culture bioreactor with surface gas exchange for the addition of oxygen, and removal of carbon dioxide. Supplemental gas sparging may be used to supply additional oxygen during the growth phase of the cell culture process and to adjust the pH with carbon dioxide during preparation of the cell culture media. The empirical determination of desired pH, osmolality and dissolved carbon dioxide level for a given mammalian cell culture process is preferably accomplished in laboratory scale bioreactors running scaled-down process conditions and may be supplemented with appropriate model-based studies.

The active control phase of the DGC process involves monitoring or measuring a plurality of parameters to be used as inputs to the microprocessor-based controller. Such inputs include the dissolved carbon dioxide levels, osmolality levels and pH level, as well as typical inputs of dissolved oxygen level, temperature, and agitation speed. Such inputs are fed to the controller at a regular interval or a continuous basis throughout the production and growth phase of the cell culture process. The microprocessor based controller receives these inputs and produces one or more output signals representing the value and setting of at least one parameter selected from the group of headspace gas composition, headspace gas flow rate, agitator speed, acid addition, base addition, or nutrient addition. The output signals are used to control or adjust the headspace gas composition, headspace gas flow rate, upward flowing agitator speed, acid addition, base addition which actively controls or maintains the dissolved carbon dioxide level, dissolved oxygen level, osmolality, or pH at the desired values or prescribed ranges for the selected cell line.

Off line measurements of residual nutrients, liquid volume, viable cell density, product concentration, etc., are used to make manual or automatic adjustment to process set points. If needed, a gas sparger may also be used to supplement the dissolved oxygen level with pure oxygen at intermittent times. As the production phase progresses, the monitoring and measuring of parameters and corresponding adjustment or control of such parameters continues until the cell culture process within the bioreactor is complete.

Figure 19A:
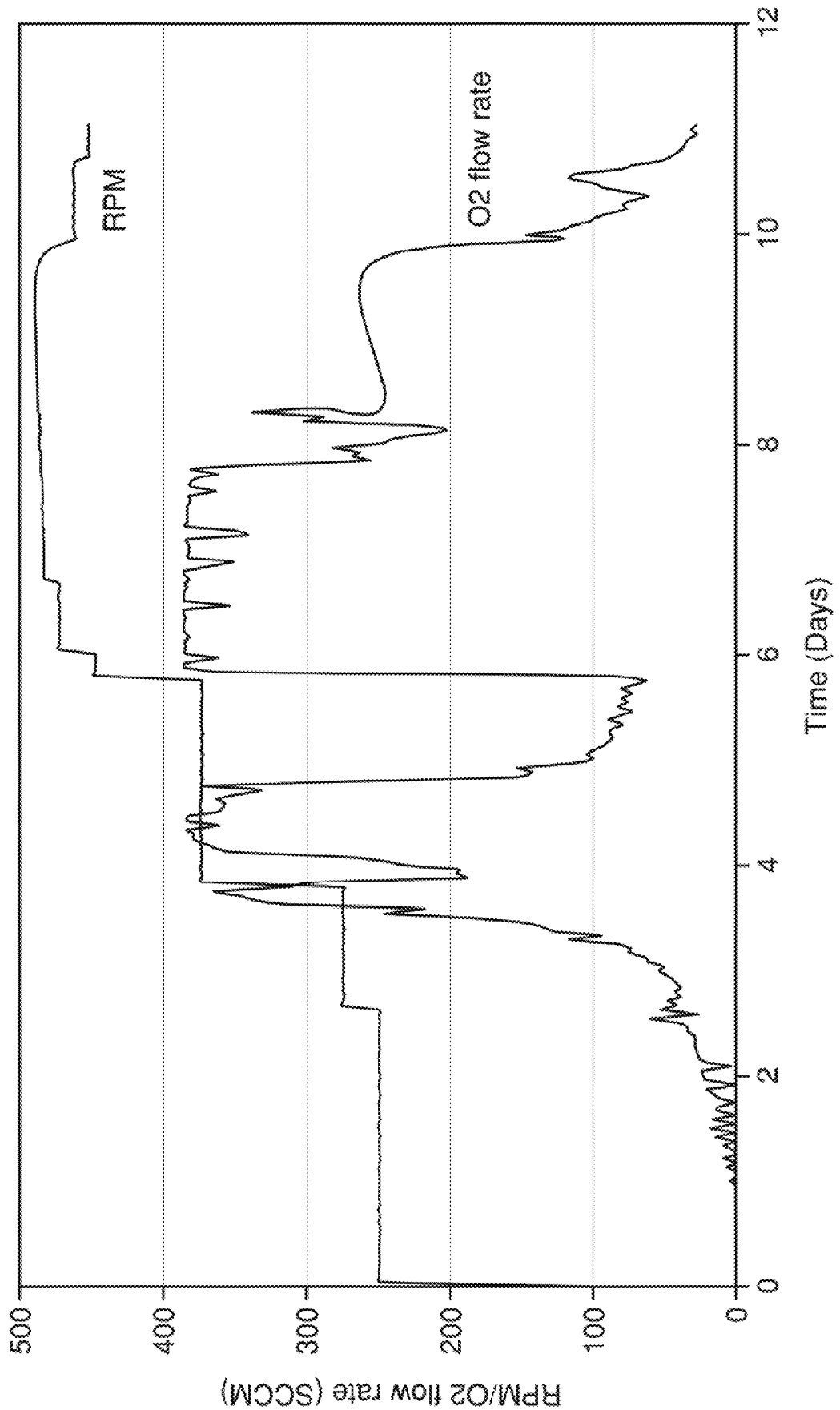
FIG. 19A is a graph that depicts the adjustments to the rotational speed of an upward flowing impeller disposed in the bioreactor and volumetric flow of an oxygen containing sweep gas in a headspace above the top surface of the cell culture medium in the bioreactor during a first sample run using the present Dynamic Gas Control (DGC) process.
Figure 19B:
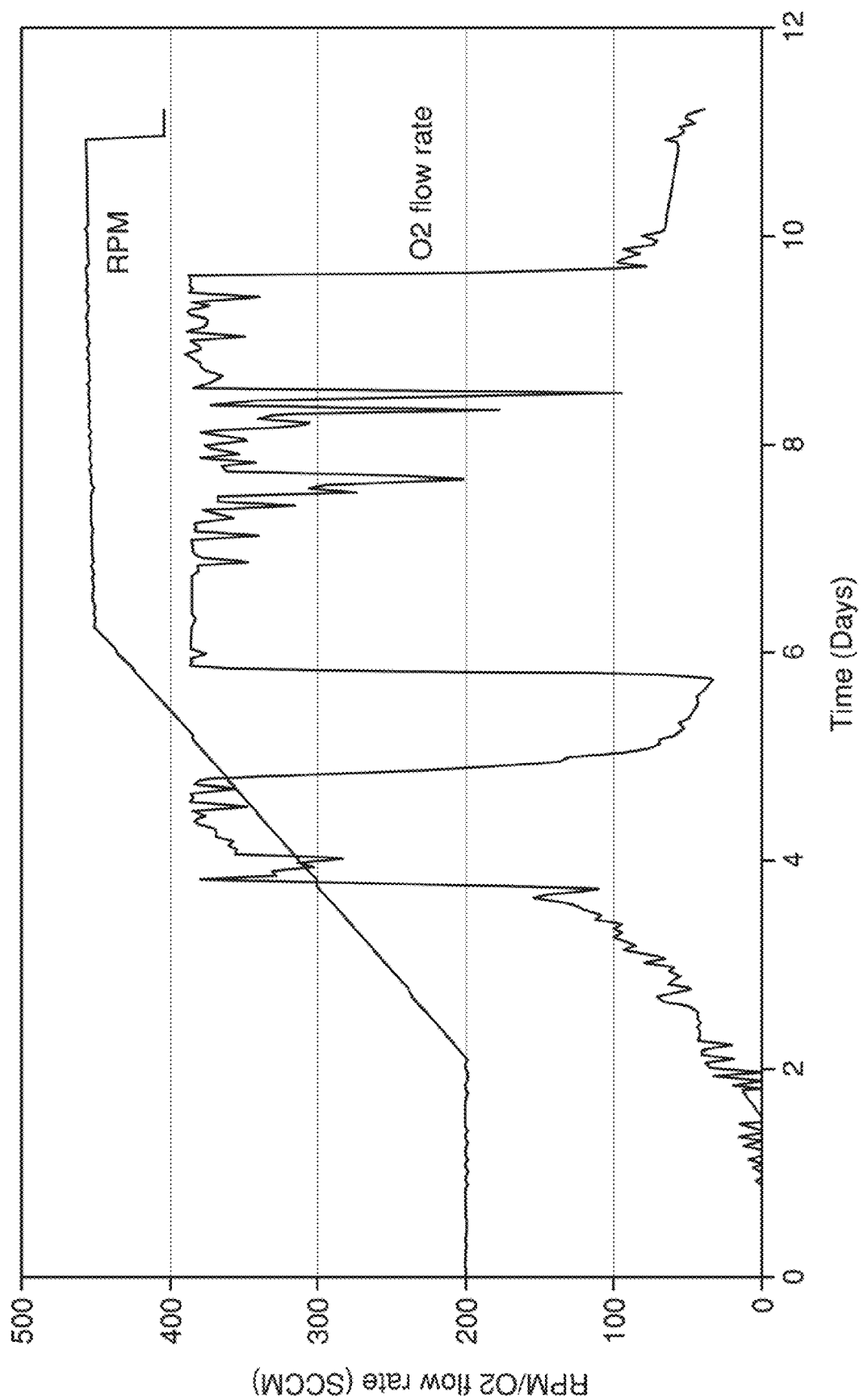
FIG. 19B is another graph that depicts the adjustments to the rotational speed of an upward flowing impeller disposed in the bioreactor and volumetric flow of oxygen containing sweep gas in a headspace above the top surface of the cell culture medium in the bioreactor during a second sample run using the present Dynamic Gas Control (DGC) process.

FIGS. 19A and 19B show typical output adjustments to the rotational speed of the upward flowing impeller or agitator and to the volumetric flow of the oxygen containing sweep gas in a headspace above the top surface of the cell culture medium in the bioreactor during the mammalian cell culture process using the Dynamic Gas Control (DCP) process.

This proposed process control scheme is applicable for nearly constant physiological temperature and also hypothermic cell culture processes. Hypothermic cell culture processes run at least part of the time at less than the typical approx. 37° C. process temperature. This proposed process control scheme is also applicable to nearly any configuration of bioreactor and operating in any mode, including batch mode, fed-batch mode, or a continuous mode of operation.

From the foregoing, it should be appreciated that the present invention thus provides various methods and systems for controlling the dissolved carbon dioxide level, pH and osmolality during a mammalian cell culture process to enhance cell viability and biologic product yield. Numerous modifications, changes, and variations of the present methods and systems will be apparent to a person skilled in the art and it is to be understood that such modifications, changes, and variations are to be included within the purview of this application.

What is claimed is:

1. A method for enhancing product yield in a mammalian cell culture process comprising the steps of:
   agitating a cell culture medium in a bioreactor using an upward flowing impeller disposed below a top surface of the cell culture medium in the bioreactor;
   adjusting the volumetric flow of an oxygen containing sweep gas in a headspace above the top surface of the cell culture medium in the bioreactor during a growth phase and a production phase of the mammalian cell culture process to maintain the concentration of dissolved oxygen in the cell culture medium in an optimum range for the mammalian cells through surface gas exchange at the top surface of the cell culture medium in the bioreactor and to maintain the dissolved carbon dioxide in the cell culture medium at a level of less than about 10% concentration of dissolved carbon dioxide throughout the growth phase and the production phase of the mammalian cell culture process by removing dissolved carbon dioxide through surface gas exchange at the top surface of the cell culture medium in the bioreactor;
   wherein the osmolality in the cell culture medium is maintained in an optimum range for the particular cells during the mammalian cell culture process and the pH of the cell culture medium is maintained in an optimum range for the particular cells during the mammalian cell culture process.

2. The method according to claim 1 wherein the concentration of dissolved carbon dioxide is stable between about 3% and 10% during the growth phase and production phase of the mammalian cell culture process.

3. The method according to claim 1 has a preferred range of osmolality is between about 300 mOsmo/kg and 700 mOsmo/kg during the growth phase and production phase of the fed-batch mammalian cell culture process.

4. The method according to claim 1 wherein the cell culture medium includes a carbon dioxide and sodium bicarbonate buffer during inoculation phase and the pH of the cell culture medium is maintained during the growth phase or production phase by adding an acid or base to the cell culture medium and wherein the addition of additional carbon dioxide gas for pH adjustment is avoided.

5. The method according to claim 1 wherein mammalian cell culture process is a fed-batch process and the osmolality in the cell culture medium increases with an addition of nutrients during the growth phase of the mammalian cell culture process and the osmolality in the cell culture medium decreases shortly thereafter.

6. The method according to claim 1 wherein the concentration of dissolved carbon dioxide and the concentration of dissolved oxygen in the cell culture medium are maintained in an optimum range by further adjusting the rotational speed of an upward flowing impeller disposed below the top surface of the cell culture medium in the bioreactor during the growth phase and production phase.

7. The method according to claim 1 wherein the mammalian cell culture process is a fed-batch process and the rise of osmolality in the cell culture medium from the beginning of the growth phase to the end of the production phase is less than about 400 mOsmol/kg.

8. The method according to claim 1 wherein the mammalian cell culture process is a fed-batch process and the rise of osmolality in the cell culture medium from the beginning of the growth phase to the production phase is less than 200 mOsmol/kg.

9. A method for enhancing product yield in a fed-batch mammalian cell culture process comprising the steps of:
inoculating a mammalian cell culture in a bioreactor with a cell culture medium that has a level of bicarbonate in equilibrium with dissolved carbon dioxide and an initial level of osmolality;
periodically adding nutrients to the cell culture medium during a growth phase of the mammalian cell culture process;
periodically adding an acid or base to the cell culture medium during the growth phase or a production phase of the mammalian cell culture process to maintain the pH level within a range for the mammalian cells without addition of carbon dioxide gas;
adjusting the volumetric flow of an oxygen containing sweep gas in a headspace above a top surface of the cell culture medium in the bioreactor during the growth phase or the production phase of the mammalian cell culture process to facilitate surface gas exchange at a top surface of the cell culture medium; and
adjusting the rotational speed of an upward flowing impeller disposed below the top surface of the cell culture medium in the bioreactor during the growth phase or production phase;
wherein the dissolved carbon dioxide in the cell culture medium is maintained at a stable level of less than about 10% concentration of dissolved carbon dioxide throughout the growth phase or the production phase of the mammalian cell culture process by stripping carbon dioxide via the surface gas exchange;
wherein the osmolality in the cell culture medium is maintained in an optimum range for the particular cells during the mammalian cell culture process.

10. The method according to claim 1 wherein the concentration of dissolved carbon dioxide is maintained at a stable level between about 3% and 10% during the growth phase and production phase of the mammalian cell culture process.

11. The method according to claim 9 has a preferred range of osmolality is between about 300 mOsmo/kg and 700 mOsmo/kg during the growth phase and production phase of the fed-batch mammalian cell culture process.

12. The method according to claim 9 wherein the concentration of dissolved oxygen the cell culture medium is maintained in an optimum range for the particular cells through surface gas exchange at the top surface of the cell culture medium in the bioreactor.

13. The method according to claim 9 wherein the top surface of the cell culture media is substantially free of foam.

14. The method according to claim 9 wherein higher cell viability is obtained earlier in the growth phase compared to a mammalian cell culture process that does not facilitate surface gas exchange at the top surface of the cell culture medium.

15. The method according to claim 9 wherein higher cell viability is obtained during the production phase compared to a mammalian cell culture process that does not facilitate surface gas exchange at the top surface of the cell culture medium.

16. The method according to claim 9 wherein the osmolality in the cell culture medium increases with an addition of nutrients and the osmolality in the cell culture medium decreases shortly thereafter.

17. A method for enhancing product yield in a fed-batch mammalian cell culture process comprising the steps of:
inoculating the cell culture with a cell culture medium that has a level of bicarbonate in equilibrium with dissolved carbon dioxide;
maintaining the concentration of dissolved carbon dioxide in the cell culture medium to less than about 10% throughout a growth phase or a production phase of the fed-batch mammalian cell culture process by removing dissolved carbon dioxide through surface gas exchange at the top surface of the cell culture medium in the bioreactor; and
limiting the rise of osmolality in the cell culture medium to less than 400 mOsmol/kg from the beginning of the growth phase to the end of the production phase of the fed-batch mammalian cell culture process;
wherein the pH of the cell culture medium is maintained in an optimum range for the particular cells during the mammalian cell culture process.

18. A method of controlling pH level of cell culture medium in a fed-batch mammalian cell culture process comprising the steps of:
providing a carbon dioxide and sodium bicarbonate buffer to cell culture medium during an inoculation phase to establish an equilibrium level of bicarbonate and dissolved carbon dioxide and initial level of osmolality in the cell culture medium;
stripping dissolved carbon dioxide from the cell culture medium during a growth phase and a production phase of the fed-batch mammalian cell culture process;
adding nutrients to the cell culture medium during the growth phase and optionally during the production phase;
adding an acid or base to the cell culture medium during the growth phase and the production phase to maintain the pH level in a range without addition of carbon dioxide gas for pH adjustment;
wherein the osmolality levels in the cell culture medium is maintained in a range and the rise of osmolality level from the beginning of the growth phase to the end of the production phase is less than 400 mOsmol/kg; and
wherein the concentration of dissolved carbon dioxide in the cell culture medium is maintained at 10% or less during the growth phase and the production phase by adjusting the volumetric flow of an oxygen containing sweep gas in a headspace above the top surface of the cell culture medium in the bioreactor to remove dissolved carbon dioxide through surface gas exchange at the top surface of the cell culture medium in the bioreactor.

19. A method for extending the cell viability and increasing protein product yield during the production phase of a fed-batch mammalian cell culture process comprising the steps of:
- diluting the cell culture medium with water during a production phase of the fed-batch mammalian cell culture process to reduce the toxic effects of waste in the cell culture medium;
- adding supplemental nutrients to the cell culture medium during the production phase of the fed-batch mammalian cell culture process to compensate for the dilution effect of the water;
- maintaining the concentration of the dissolved carbon dioxide in the cell culture medium to 10% or less and maintaining both osmolality level and pH level in the cell culture medium within an optimum range for the mammalian cells during the production phase of the fed-batch mammalian cell culture process by adjusting the volumetric flow of an oxygen containing sweep gas in a headspace above the top surface of the cell culture medium in the bioreactor to remove dissolved carbon dioxide through surface gas exchange at the top surface of the cell culture medium in the bioreactor;
- wherein the protein product yield is increased due to the extended cell viability of the mammalian cells during the production phase of the fed-batch mammalian cell culture process.

20. A method for improving purity of a protein product produced from a fed-batch mammalian cell culture process comprising the steps of:
- inoculating a mammalian cell culture in a bioreactor with a cell culture medium that has a level of bicarbonate in equilibrium with dissolved carbon dioxide and an initial level of osmolality;
- adding nutrients to the cell culture medium thereby increasing the osmolality level of the cell culture medium to accelerate protein production from the mammalian cells;
- adding an acid or base to the cell culture medium to maintain the pH level within a range for the mammalian cells;
- stripping dissolved carbon dioxide from the cell culture medium throughout the fed-batch mammalian cell culture process wherein the concentration of dissolved carbon dioxide in the cell culture medium is maintained at 10% or less through surface gas exchange at the top surface of the cell culture medium in the bioreactor;
- wherein the rise in osmolality level from the initial level of osmolality is limited to less than 400 mOsmol/kg; and
- harvesting the protein product from the bioreactor during the growth phase or early production phase of the fed-batch mammalian cell culture process.

21. A method of controlling the osmolality level of cell culture medium in a fed-batch mammalian cell culture process comprising the steps of:
- providing a carbon dioxide and sodium bicarbonate buffer to cell culture medium during an inoculation phase to establish an equilibrium level of bicarbonate and dissolved carbon dioxide and initial level of osmolality in the cell culture medium;
- adding nutrients to the cell culture medium during a growth phase thereby increasing the osmolality level of the cell culture medium;
- adding an acid or base to the cell culture medium during the growth phase to maintain the pH level in a range;
- stripping dissolved carbon dioxide from the cell culture medium during the growth phase of the fed-batch mammalian cell culture process wherein the concentration of dissolved carbon dioxide in the cell culture medium is maintained at 10% or less during the growth phase through surface gas exchange at the top surface of the cell culture medium in the bioreactor;
- wherein the osmolality levels in the cell culture medium decreases during portions of the growth phase and the total rise of osmolality level from the beginning of the growth phase to the end of the growth phase is less than about 400 mOsmol/kg.

* * * * *